(12) United States Patent
Miller et al.

(10) Patent No.: US 6,709,442 B2
(45) Date of Patent: Mar. 23, 2004

(54) VASCULAR BYPASS GRAFTING INSTRUMENT AND METHOD

(75) Inventors: Arnold Miller, Chestnut Hill, MA (US); William J. Allen, Stratford, CT (US)

(73) Assignee: Onux Medical, Inc., Hampton, NH (US)

( * ) Notice: Subject to any disclaimer, the term of this patent is extended or adjusted under 35 U.S.C. 154(b) by 11 days.

(21) Appl. No.: 09/944,840

(22) Filed: Aug. 31, 2001

(65) Prior Publication Data

US 2002/0065524 A1 May 30, 2002

Related U.S. Application Data

(60) Provisional application No. 60/229,675, filed on Sep. 1, 2000.

(51) Int. Cl.$^7$ ............................................. A61B 17/04
(52) U.S. Cl. ........................ 606/153; 606/139; 606/144
(58) Field of Search ................................ 606/153, 144, 606/148, 139

(56) References Cited

U.S. PATENT DOCUMENTS 4,366,819 A * 1/1983 Kaster ........................ 606/153
4,485,816 A   12/1984 Krumme
4,665,906 A    5/1987 Jervis (List continued on next page.)

FOREIGN PATENT DOCUMENTS

WO    WO 00/16701 A1    3/2000

*Primary Examiner*—Michael J. Milano
*Assistant Examiner*—Bradford C Pantuck
(74) *Attorney, Agent, or Firm*—Pandiscio & Pandiscio

(57) ABSTRACT

An instrument for attaching a graft to an aorta includes a first needle assembly for breaching the aorta to provide a hole in a wall thereof, and a carrier portion for insertion of an end of a tubular graft through the hole and into the aorta. Arms are pivotally mounted on the instrument and are moveable from a position extending axially of the carrier to a position extending radially from the carrier to spread the end of the graft radially outwardly from a tubular portion of the graft to form an annular flange extending outwardly from the tubular portion, and to support the flange within the aorta and around the hole therein. A second needle assembly retains the suture material and advances the suture material into engagement with the aorta wall and the graft flange for suturing the graft flange to the aorta wall.

23 Claims, 19 Drawing Sheets

U.S. PATENT DOCUMENTS

| | | | |
|---|---|---|---|
| 4,669,473 A | 6/1987 | Richards et al. | |
| 5,002,563 A | 3/1991 | Pyka et al. | |
| 5,067,957 A | 11/1991 | Jervis | |
| 5,078,726 A | 1/1992 | Kreamer | |
| 5,190,546 A | 3/1993 | Jervis | |
| 5,219,358 A | 6/1993 | Bendel et al. | |
| 5,258,000 A | 11/1993 | Gianturco | |
| 5,259,394 A | 11/1993 | Bens | |
| 5,540,701 A | 7/1996 | Sharkey et al. | |
| 5,575,800 A | 11/1996 | Gordon | |
| 5,582,616 A | 12/1996 | Bolduc et al. | |
| 5,597,378 A | 1/1997 | Jervis | |
| 5,601,572 A | 2/1997 | Middleman et al. | |
| 5,626,588 A | 5/1997 | Sauer et al. | |
| 5,695,504 A * | 12/1997 | Gifford et al. | 606/153 |
| 5,782,844 A | 7/1998 | Yoon et al. | |
| 5,810,851 A | 9/1998 | Yoon | |
| 5,810,882 A | 9/1998 | Bolduc et al. | |
| 5,830,221 A | 11/1998 | Stein et al. | |
| 5,836,955 A * | 11/1998 | Buelna et al. | 606/148 |
| 5,843,164 A | 12/1998 | Frantzen et al. | |
| 5,868,762 A * | 2/1999 | Cragg et al. | 606/144 |
| 5,944,750 A * | 8/1999 | Tanner et al. | 623/1.23 |
| 5,954,732 A * | 9/1999 | Hart et al. | 606/144 |
| 5,957,940 A * | 9/1999 | Tanner et al. | 606/155 |
| 5,972,001 A | 10/1999 | Yoon | |
| 5,984,917 A | 11/1999 | Fleischman et al. | |
| 5,997,556 A * | 12/1999 | Tanner | 606/153 |
| 6,113,611 A * | 9/2000 | Allen et al. | 606/151 |
| 6,132,438 A | 10/2000 | Fleischman et al. | |
| 6,193,734 B1 | 2/2001 | Bolduc et al. | |
| 6,254,618 B1 * | 7/2001 | Dakov | 606/153 |
| 6,287,317 B1 | 9/2001 | Makower et al. | |
| 6,306,141 B1 | 10/2001 | Jervis | |
| 6,346,111 B1 | 2/2002 | Gordon et al. | |
| 6,358,258 B1 | 3/2002 | Arcia et al. | |
| 6,379,366 B1 | 4/2002 | Fleischman et al. | |
| 6,416,522 B1 | 7/2002 | Strecker | |
| 6,416,535 B1 * | 7/2002 | Lazarus | 623/1.11 |
| 6,592,593 B1 * | 7/2003 | Parodi et al. | 606/108 |
| 2002/0029048 A1 * | 3/2002 | Miller | 606/138 |
| 2003/0033005 A1 * | 2/2003 | Houser et al. | 623/1.35 |

* cited by examiner

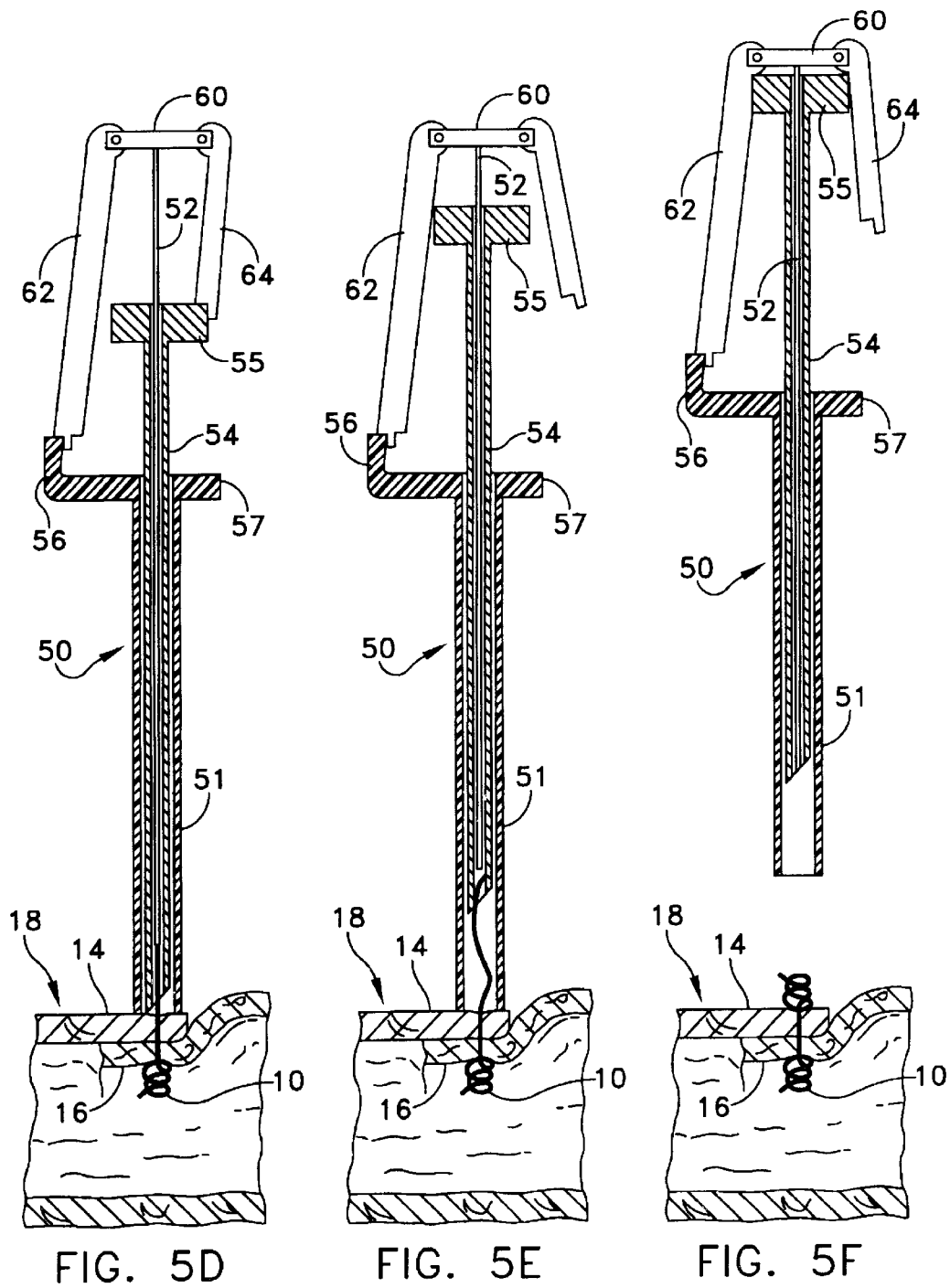

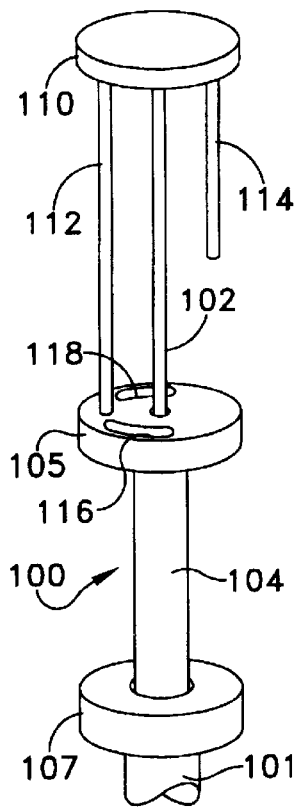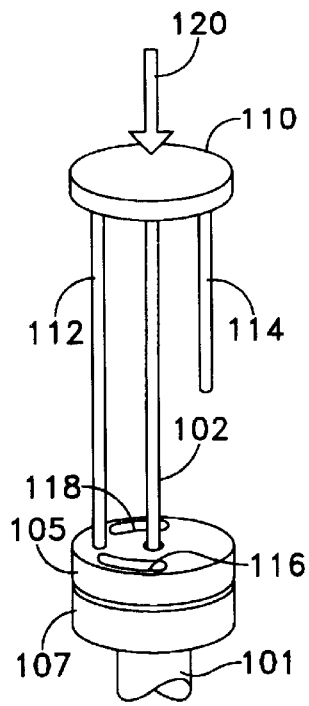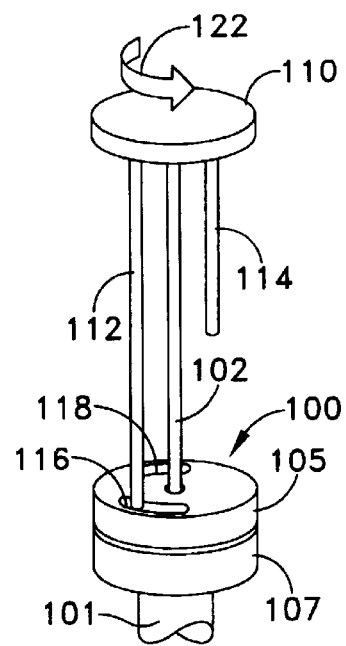
FIG. 6A  FIG. 6B  FIG. 6C
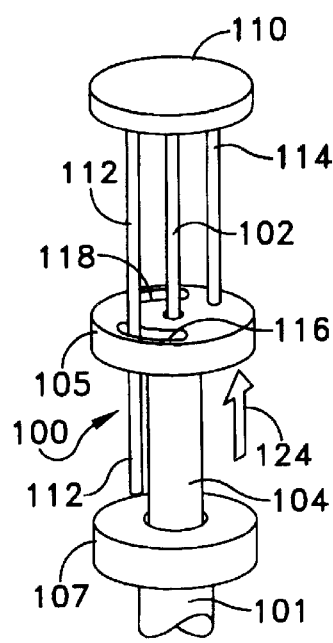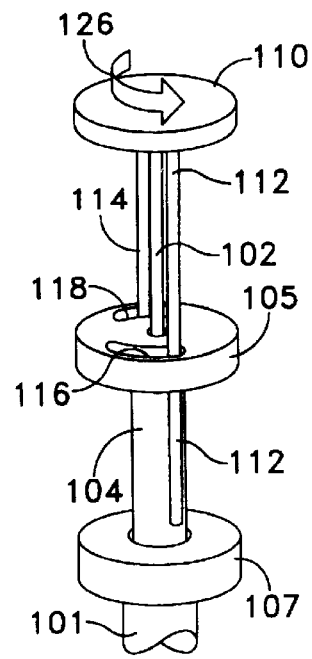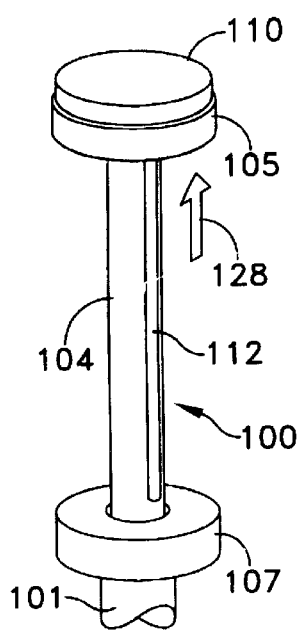
FIG. 6D  FIG. 6E  FIG. 6F

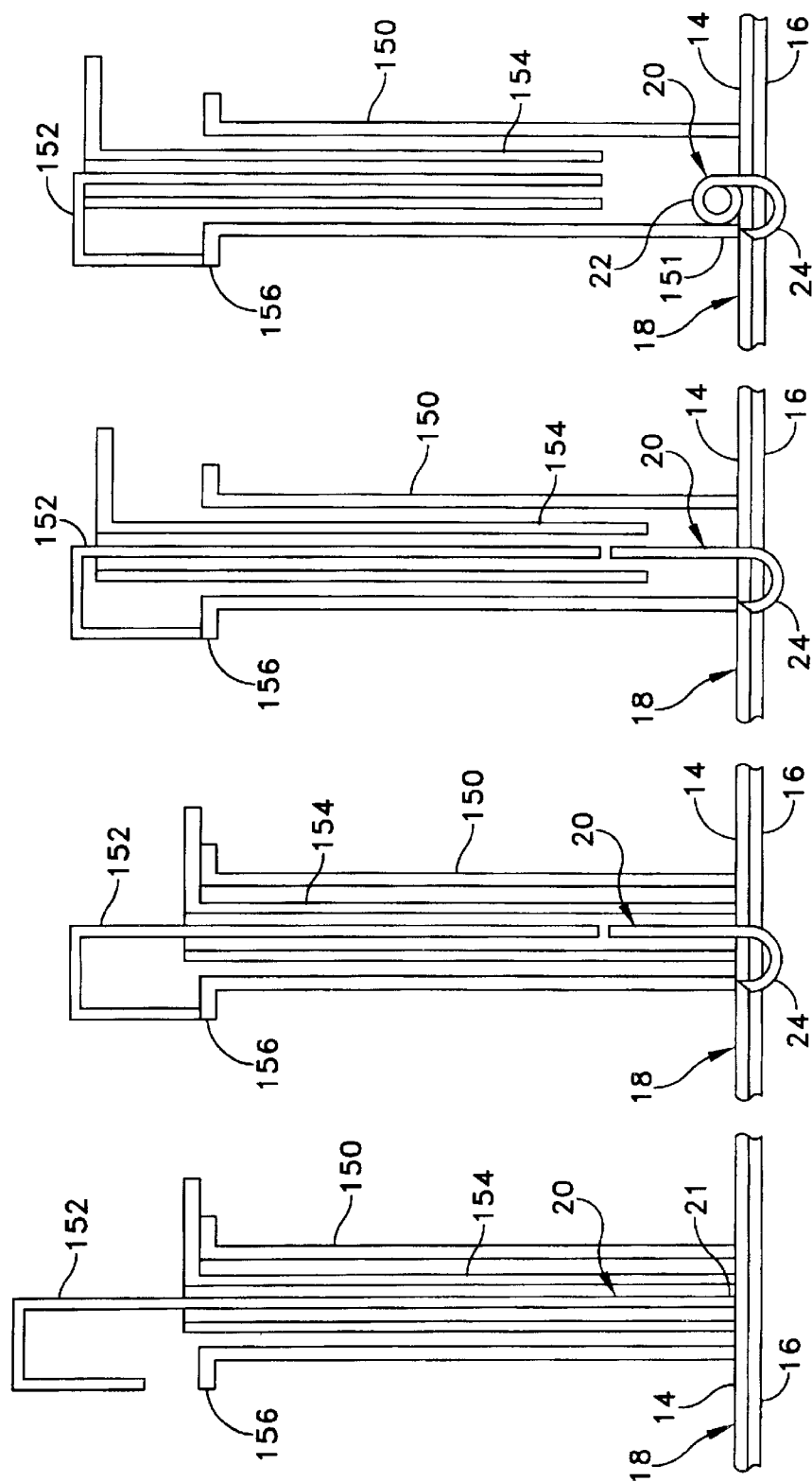

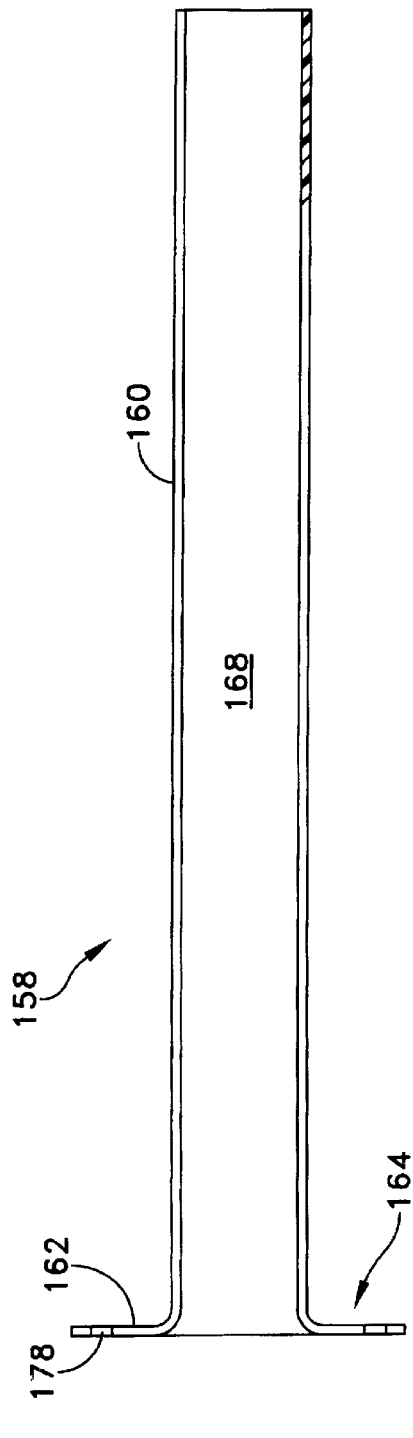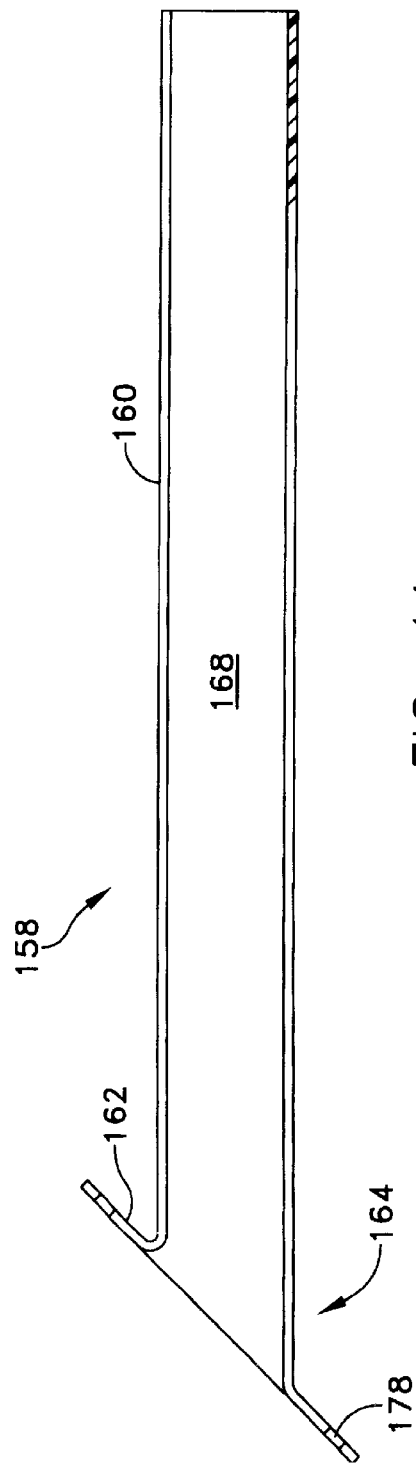

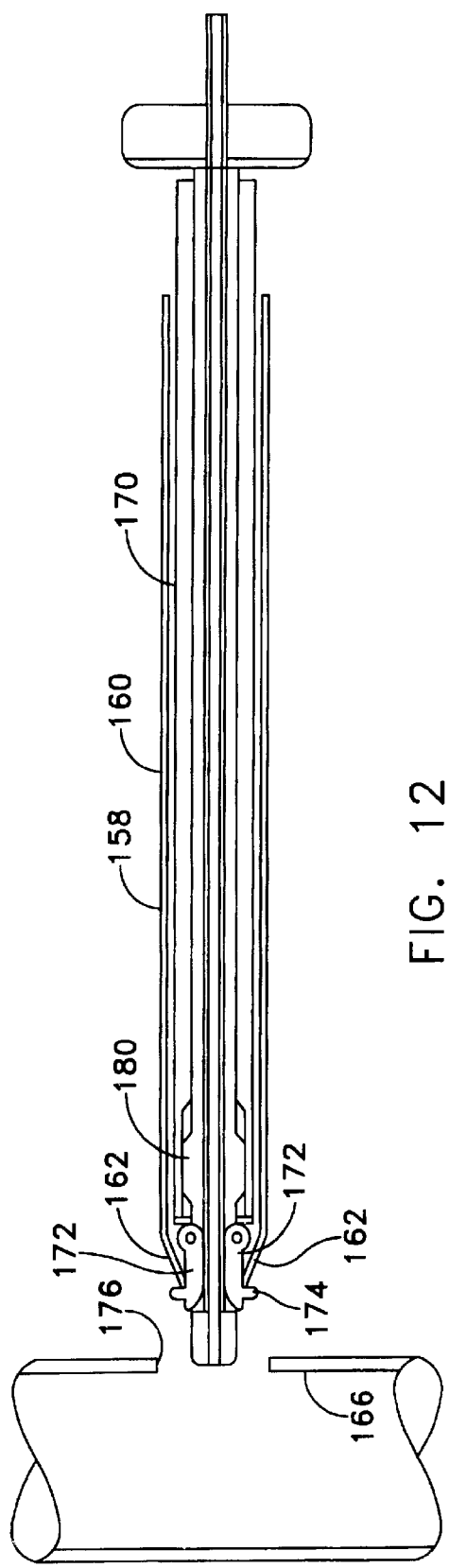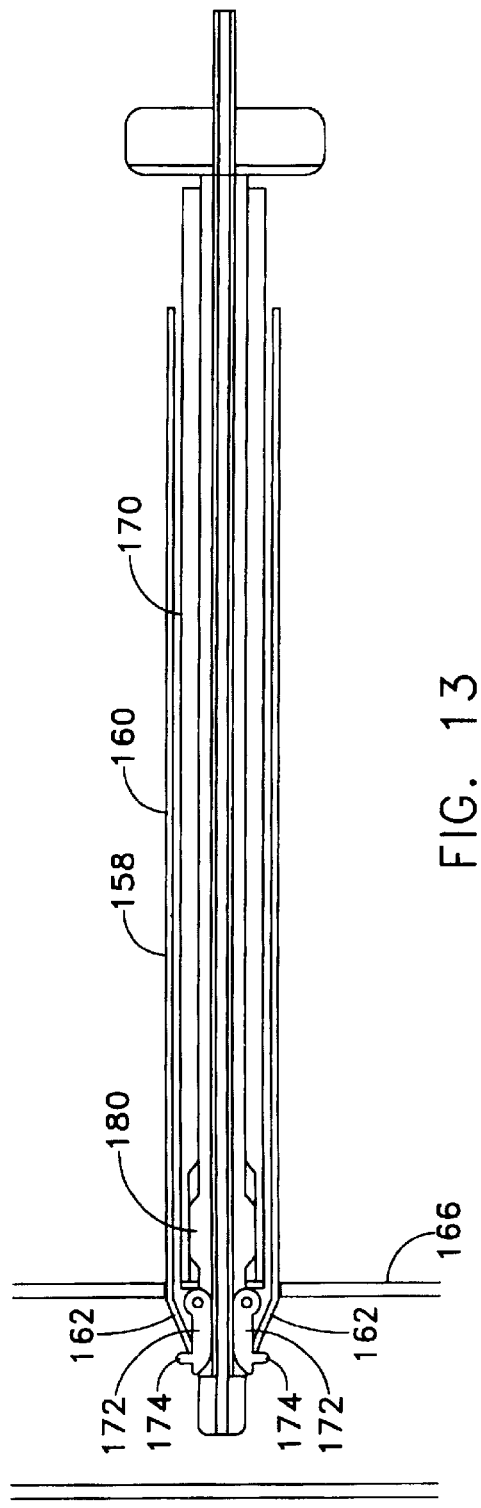
FIG. 12
FIG. 13

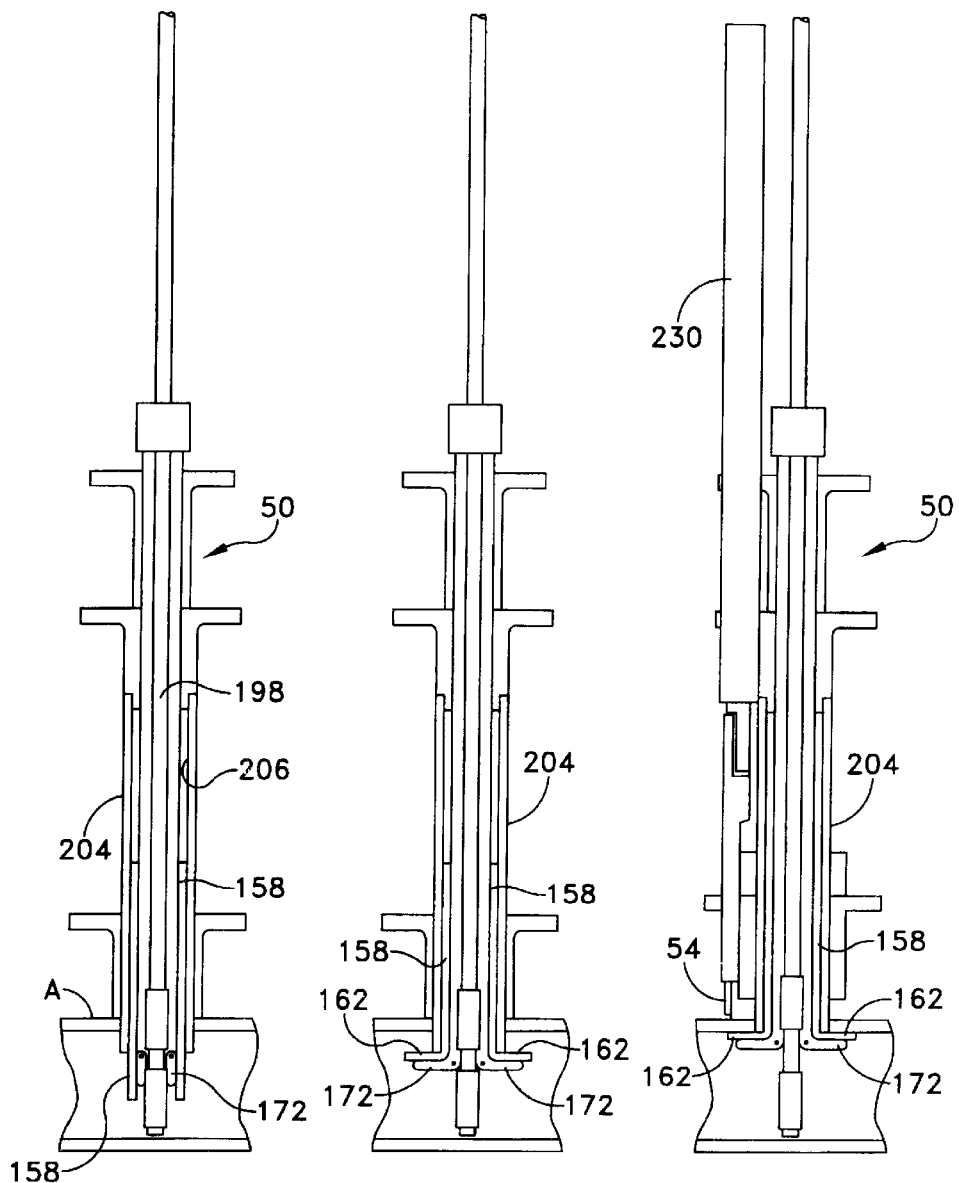

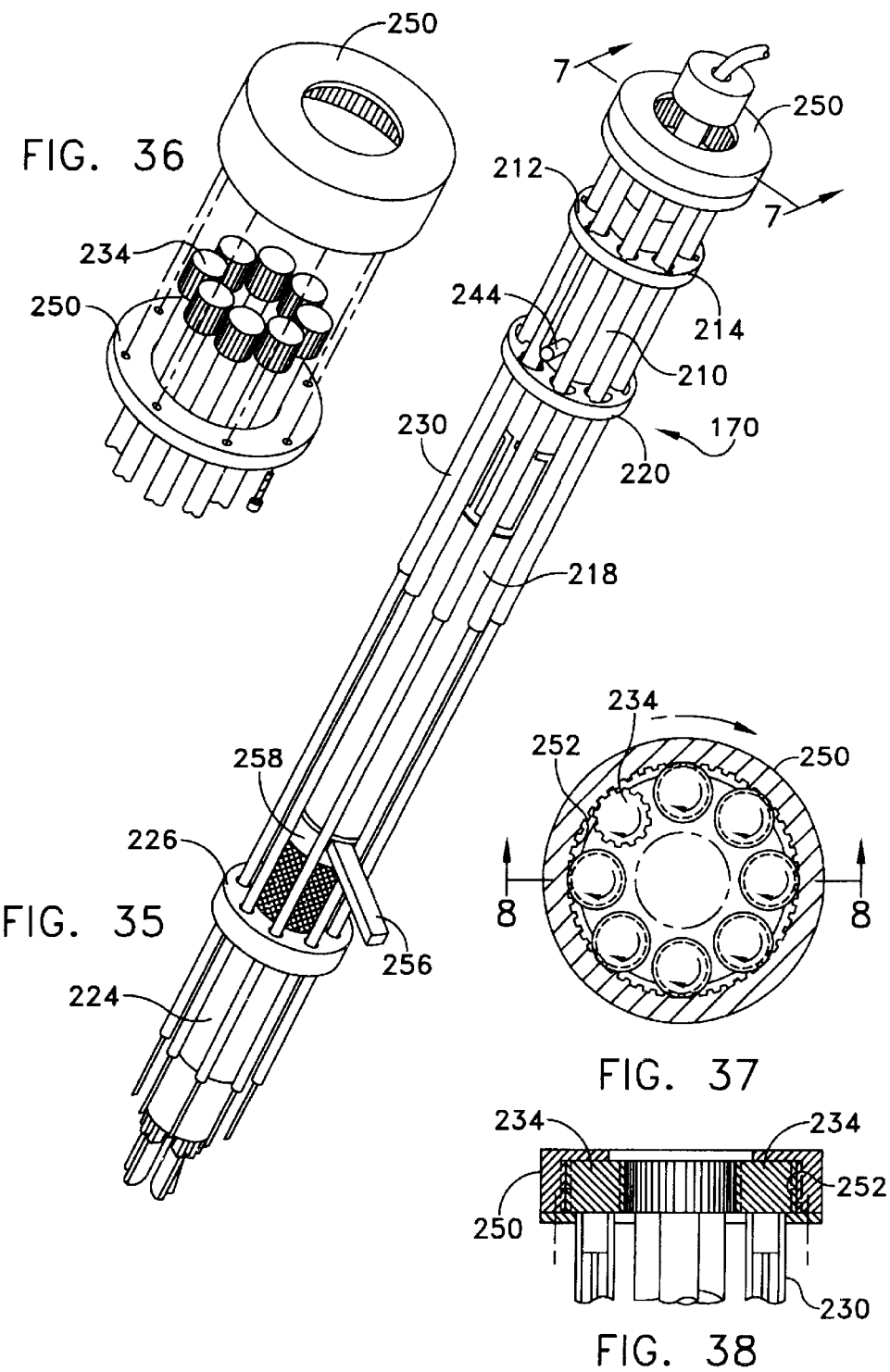

VASCULAR BYPASS GRAFTING INSTRUMENT AND METHOD

REFERENCE TO PENDING PRIOR PATENT APPLICATION

This patent application claims benefit of pending prior U.S. Provisional Patent Application Ser. No. 60/229,675, filed Sep. 1, 2000 by William J. Allen et al. for VASCULAR BYPASS GRAFTING SYSTEM, which patent application is hereby incorporated herein by reference.

FIELD OF THE INVENTION

The invention relates to a fastener and a delivery instrument for joining multiple layers of thin flexible material. More particularly, the invention relates to a surgical fastener and a delivery instrument and method for joining living tissue and/or synthetic materials which may be used as a substitute for tissue.

Still more specifically, the invention relates to a system for joining large grafts to the human aorta less invasively and with substantially less blood loss than is typically experienced in this type of operation. The invention further permits the graft to be anastomosed to the aorta without temporarily stopping the flow of blood distal to the operating site. The combination of a less invasive, less traumatic, procedure provides the surgeon with more freedom in choosing the most appropriate site in which to attach the graft.

BACKGROUND OF THE INVENTION

Historically, living tissue has been most commonly surgically repaired by thread, such as a suture, introduced by a pointed metal needle and tied with just enough tension to establish hemostasis, or control of bleeding, by compressing the tissue. Correct tension is established by the surgeon based on observation and. judgment derived from extensive training. Excess tension can cause necrosis (the localized death of living tissue) and eventual failure of the repair.

An alternative method of joining tissue using metal staples has evolved over the last 90 years to a point where specialized staples for both skin and internal tissue closure are in common use today. The staples., which have sharp points for penetrating tissue, are formed in place by delivery instruments which bend them to a permanent shape suitable for tissue retention. The delivery instruments include mechanisms, such as an anvil, which control to some extent the relationship between tissue and staple, including the compression necessary to control bleeding. To the extent that they do so, surgeon skill is less of a factor in successful wound closure.

For conventional surgery, the clinical results for suturing and stapling are essentially the same, but both have their disadvantages. Sutures are suitable for all types of wound closure, but require that the surgeon have adequate access to the wound site and possess the skill to choose and apply the suture correctly. Conventional staples can also be appropriate for internal use, but require that a strong, rigid anvil be placed behind the tissues to be joined. Furthermore, the application of staples requires that there be enough space for an instrument, which can produce the necessary force to form the staple against the anvil. Stapling, however, is generally faster and, as previously noted, requires a lower level of skill.

The recent development of a beneficial, less invasive technique for gall bladder removal has suggested the feasibility of other abdominal procedures, such as a bowel and hernia repair, that require the remote application of an internal fastener. As a result, less invasive instruments have been developed for both suturing and stapling remotely from the wound site by the surgeon. At the same time, patient benefit considerations are driving the development of less invasive techniques for a full range of abdominal and thoracic procedures including coronary artery bypass and valve replacement.

To date, stapling has proven to be more suitable for less invasive surgery than suturing. Instruments developed for that purpose approximately replicate the functions of staplers developed for open surgery and are approximately as easy to use. Instruments developed for less invasive suturing, on the other hand, are slow and cumbersome and do not solve the essential problem of tensioning the suture and tying the knot remotely. Sutures will find limited use in less invasive surgery but it is most likely that related wound closure problems beyond the capability of conventional staples will be solved by innovative mechanical fasteners which can more easily be remotely applied.

For instance, a new fastener has been designed for less invasive hernia repair in which a synthetic mesh is used to reinforce the repair by anchoring it to surrounding tissue. Suturing is feasible but difficult. Conventional stapling is not feasible because an anvil cannot access the distal side of the tissue. The new fastener has the shape of a coil spring with the wire sharpened at one end and has been used successfully to attach the mesh by screwing the coil through it into the tissue. This new fastener can access the wound site through a small port in the abdominal wall. This fastener, however, does not produce compression upon the synthetic and natural tissue layers and thus does not produce hemostasis because the fastener is screwed into the wound site in its natural shape. Because this fastener does not produce hemostasis, it may not be suitable for a wide range of surgical applications.

Other surgical fasteners have been fabricated from shape memory alloy. U.S. Pat. No. 4,485,816 to Krumme discloses a shape-memory surgical staple that uses an electric current to heat the staple to make it close. U.S. Pat. No. 5,002,562 to Pyka et al. discloses a fastener made from shape memory alloy that has the shape of a suturing loop in its unreformed shape. As noted above, however, sutures and staples are not always desirable for all surgical applications.

It is believed that other applications exist or will be identified for fastening layers of tissue where anvil access is not practical and where compression must be applied to the tissue to achieve hemostasis. For example, these criteria apply to the attachment of a graft more or less at right angles to another, larger, blood vessel ("end to side" anastomosis) such as the aorta for vascular bypass purposes. The availability of a less invasive vascular bypass procedure implies a significant patient benefit. Another example is the use of the fastener in endovascular procedures to attach a graft within large vessels such as the aorta, iliac or femoral arteries to repair aneurysms and occlusions. Stents, which are currently used for this purpose, are often insufficiently compliant to prevent leakage and consequent failure of the repair. Direct fixation of the graft to the inner wall of the vessel by the fasteners described herein may overcome this inherent problem of current techniques for endovascular repair.

What is desired, therefore, is a mechanical fastener and deployment instrument that can access internal tissue through a small surgical access port or incision and that can be applied conveniently and remotely.

With respect to the aforesaid joining of grafts to a human aorta, grafts, usually synthetic, are commonly used to surgically bypass major arteries which are critically blocked by occlusive disease. These include, but are not limited to, femoral, iliac, renal and other visceral arteries. In this procedure, as practiced conventially, the graft is joined to the aorta at a convenient place (one which is surgically accessible, not calcified and reasonably close to the blockage), and connected to the diseased vessel at a point distal to the blockage. These secondary vascular connections (anastomoses) are made using conventional sutures to provide mechanical strength and control of bleeding (hemostasis). Large grafts are also used to bypass aneurysms or weaknesses in the walls, of major arteries to forestall an emergency or life threatening condition. After bypass, the diseased portion of the artery is blocked to isolate it from the stress of arterial pressure. There are problems associated with both of these bypass techniques. In general, the most difficult part of the procedure with respect to the human aorta is in making the initial connection to the wall of the aorta. In essence, a hole the size of the graft is made in the wall with the aorta temporarily blocked. The graft is then carefully sutured to the periphery of the hole. The blocking clamp is then removed and flow through the aorta is reestablished. The potential for blood loss is significant due to the large volume of blood and relatively high systolic pressure in the aorta. In addition, the need to use a blocking clamp to prevent blood loss introduces a significant strain on the heart.

There is thus a need for an instrument to deliver the graft, and a procedure for puncturing the aorta and making an anastomosis quickly and reliably through a small incision with minimal loss of blood.

SUMMARY OF THE INVENTION

Accordingly, an object of the present invention is to provide a surgical fastener that can access internal tissue through a small surgical access port or incision.

It is a further object of the present invention to provide a surgical fastener that can be applied remotely.

It is yet another object of the present invention to provide a surgical fastener that uses the superelastic properties of shape memory alloy without having to apply heat to the fastener.

It is still another object of the present invention to provide a deployment instrument that can be used to deploy the surgical fasteners of above.

A still further object of the present invention is to provide an improved instrument and method for delivering a graft to the operative site, puncturing the aorta, and making an anastomosis quickly and reliably through a small incision, and with minimal loss of blood and reduced heart strain.

These objects of the invention are achieved by a surgical fastener preferably made from a shape memory alloy that accesses internal tissue or other synthetic material through a small surgical access port or incision. After the fastener is deployed through layers of tissue, it assumes a shape that automatically applies to the layers of tissue an appropriate hemostatic compression which is relatively independent of tissue thickness. The fastener is a suitable replacement for conventional non bio-absorbable sutures and staples in certain clinical applications. Its shape, method of deployment, and low force requirements make it suitable for standard surgical procedures and especially suitable for laparoscopic and other less invasive surgery where access to the wound site is limited, including endovascular surgery. The invention is expected to be especially useful for attaching synthetic grafts to an aorta.

In accordance with a further feature of the invention, there is provided an instrument for attaching a graft to an aorta or other tubular structure. The instrument comprises a first needle assembly for breaching the aorta to provide a hole in a wall thereof, a carrier portion for insertion of an end of a tubular graft through the hole and into the aorta, arms pivotally mounted on the instrument and moveable from a position extending axially of the carrier to a position extending radially from the carrier to spread the end of the tubular graft radially outwardly from a tubular body portion of the graft to form a generally annular flange portion extending outwardly from the tubular body portion, and to support the flange portion within the aorta and around the hole therein. A second needle assembly is adapted to retain suture material (e.g., the aforementioned surgical fastener) therein and to advance the suture material into engagement with the aorta wall and the graft flange portion for suturing the graft flange portion to the aorta wall.

In accordance with a still further feature of the invention, there is provided a method for fixing a graft to an aorta or other tubular structure. The method comprises the steps of providing a graft having a tubular body portion and an annular flange portion at one end of the tubular body portion, providing an instrument for breaching the aorta, positioning the flange portion of the graft adjacent a wall of the aorta, and suturing (e.g., with the aforementioned surgical fastener) the graft flange portion to the aorta. The method includes mounting the graft in the instrument, and mounting a needle assembly, supporting suturing material, on the instrument. The method further includes operating the instrument to breach (i) the aorta to provide a hole therein, (ii) to move the graft to engage the aorta around the hole therein with the graft flange portion, (iii) to provide anvil support to the graft flange portion within the aorta, and (iv) to effect suturing of the graft flange onto the aorta around the hole in the aorta.

The above and other features of the invention, including various novel details of construction and combinations of parts and method steps will now be more particularly described with reference to the accompanying drawings and pointed out in the claims. It will be understood that the particular devices and method steps embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIGS. 5A–5F are front cutaway views of a deployment instrument showing the insertion of the surgical fastener of FIG. 1;

FIGS. 6A–6F are front isometric views of another embodiment of a deployment instrument showing the insertion of a surgical fastener;

FIGS. 9A–9D are side cutaway views showing the use of a deployment instrument with the surgical fastener of FIG. 2;

FIG. 10 is a centerline sectional view of a graft suitable for attachment to an aorta;

FIG. 11 is similar to FIG. 10 but illustrative of an alternative embodiment of graft;

FIGS. 12–17 are diagrammatic sequential sectional views, illustrating the attachment of a graft to an aorta;

FIGS. 19–33 are diagrammatic sequential sectional views, illustrating an alternative method for attachment of a graft to an aorta;

FIGS. 34–36 are perspective views of an alternative embodiment of an instrument for attaching a graft to an aorta;

FIG. 37 is a sectional view taken along line 7—7 of FIG. 35; and

FIG. 38 in a sectional view taken along line 8—8 of FIG. 37.

DETAILED DESCRIPTION OF THE PREFERRED EMBODIMENTS

Surgical fasteners, each in accordance with the invention, are shown in FIGS. 1A–4. The surgical fastener is preferably a one piece metal or plastic element appropriately configured during manufacture to hold layers of tissue in compression. To apply the fastener, as shown in FIGS. 5A–5F, 6A–6F, and 9A–9D, a needle assembly comprising a straight tube or needle included in a delivery mechanism is preferably used to hold and deflect the fastener from its final shape into a straight configuration. In application, the tube is either inserted through the tissue or held against the tissue to be joined and the fastener is pushed from the tube until the fastener penetrates the tissue and gradually assumes its original shape, trapping and compressing the layers of tissue 18 between its various elements.

In order to straighten the various surgical wire fasteners described herein without permanent deformation, a superelastic alloy of nickel and titanium is preferably used to make the fasteners. The fastener is preferably made from a commercial material Nitinol, which is referred to as a "shape memory alloy." Superelasticity can be conveniently likened to memory. Although forced into a straight line after forming, the superelastic fastener is able to "remember" its former shape and to return to it when no longer constrained within a straight tube. Nitinol in superelastic form has an extremely high elastic limit, which allows large amounts of bending without permanent deformation. In general, Nitinol is capable of strain ratios of up to 8% without experiencing permanent deformation. For round wire, the fastener is designed to function within the limits of d/2R equal to or less than 0.08, where d is the diameter of the wire and R is the radius to which the wire is formed. It should be noted that the fastener described herein can be made from any material so long as it is adequately elastic. Preferably, the material has superelastic characteristics.

Figure 1A:
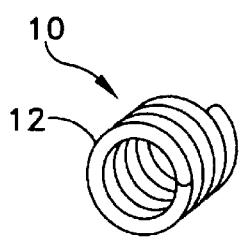
FIGS. 1A, 1B and 1C are an isometric view and two side views, respectively, of a first embodiment of the surgical fastener in accordance with the invention.
Figure 1B:
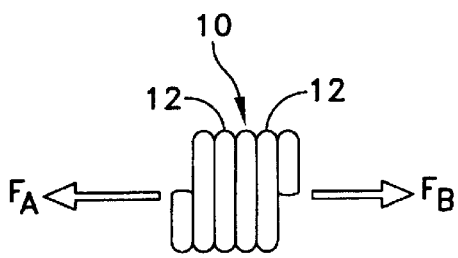
Figure 1C:
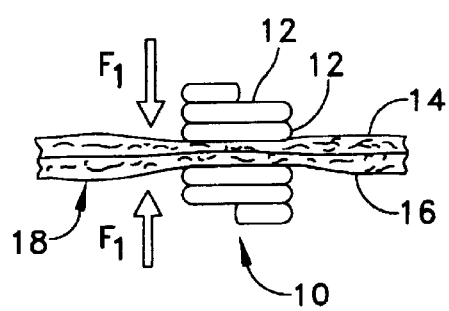

The preferred embodiment of the fastener 10, shown in FIGS. 1A–1C, is essentially that of the body of an extension spring having coils 12. At rest, the coils of this fastener 10 are spring biased toward each other so that a force $F_A$ is required to effect separation of the coils. The force at which the coils just begin to separate is the preload value for the fastener. Additional force causes separation of the coils 12 as a function of the gradient of the fastener. Shown in FIG. 1C, layers of tissue 18 that are trapped between adjacent coils 12 of the fastener will be clamped with a force $F_1$ being substantially normal to the surface of the tissue 18 and having a value somewhat higher than the preload value of the fastener. This force, which is a function of fastener material, dimensions and winding technique, is chosen to insure hemostasis when vascular tissue is to be clamped. It should be noted that a compression spring could be used in place of an extension spring so long as the tissue is thick enough that it is compressed between the coils of the fastener once it is in place. The theory and practice of winding preloaded coils of metallic wire is routinely practiced in the manufacture of extension springs and is well known to those skilled in the art.

When the fastener of FIGS. 1A–1C is made of a superelastic material and the strain ratio limitation described above is observed, the fastener can be straightened to penetrate tissue 18 and then released to allow its coils to reform on both the proximate 14 and distal 16 sides of the tissue, thereby clamping the tissue between two coils. The number of coils 12 is not especially critical. At least two full coils 12 are required and more, such as four coils, are preferable to make placement in the tissue less critical. The coils 12 preferably have a diameter of ³⁄₁₆ to ¼ of an inch. Preferably, the end of the fastener inside of the body rests flush next to the adjacent coil so that the body will not be injured from the fastener end.

Figure 2:
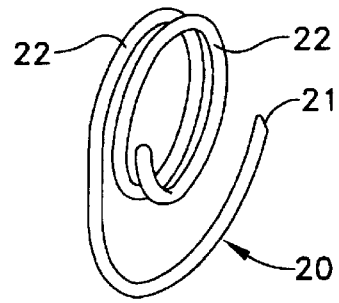
FIG. 2 is an isometric view of a second embodiment of the surgical fastener in accordance with the invention.
Figure 3:
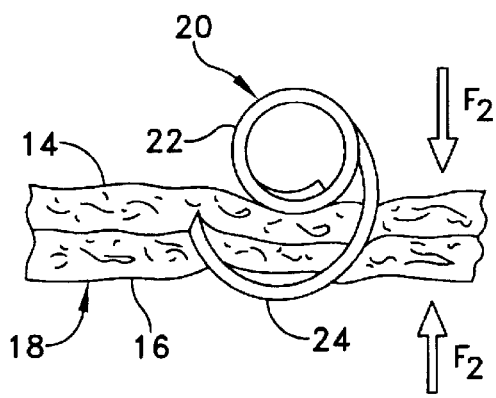
FIG. 3 is a side cutaway view of the second embodiment of the surgical fastener of FIG. 2 in accordance with the invention.

FIGS. 2 and 3 show another embodiment of the fastener 20 before and after installation in two layers 14, 16 of tissue 18. The presence of the tissue layers prevents the fastener from returning completely to its original state. The force required to spread the spring biased fastener apart by this amount therefore also represents the substantially normal compressive force $F_2$ applied to the layers of tissue 18. That force, which is a function of wire diameter and fastener geometry, is chosen by design to achieve homeostasis. Those parameters also determine the gradient or stiffness of the fastener as measured in terms of force $F_2$ versus deflection of the fastener. Since different tissue thicknesses produce different deflections, and therefore different compressive forces, the gradient must be sufficiently low to maintain reasonable hemostasis over the normal range of tissue thickness without inducing necrosis.

FIG. 2 is an isometric view of the fastener 20 shown schematically in FIG. 3. The lower coil 24 penetrates the tissue and curves in a half circle to re-enter the tissue layers. The upper coils 22 bear on the tissue and tend to trap it inside of the larger lower coil. The number of upper coils 22 can vary without altering the essential behavior of the fastener 20. Preferably, two or more coils 22 are used to help distribute clamping forces more uniformly about the lower coil, thereby preventing misorientation of the fastener 20 in the tissue 18.

Figure 4:
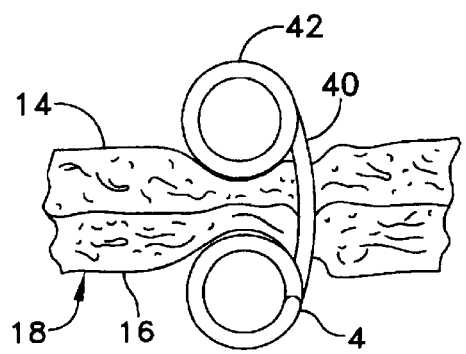
FIG. 4 a side cutaway view of a third embodiment of the surgical fastener in accordance with the invention.

The fastener 40 in FIG. 4 has symmetrical coils to distribute stress uniformly on both sides of the tissues to be joined.

The fasteners in FIGS. 2–3 and 4 are similar to the fastener in FIGS. 1A–1C in that they are spring biased and use coils to apply pressure. The coils in FIGS. 2–3 and 4 each have an axis that is oriented substantially transverse to the direction that the fastener takes when it is in a straightened form, whereas the coils in FIGS. 1A–1C each have an have an axis that is substantially transverse to its straightened form.

The fasteners in FIGS. 1C, 3 and 4 all show a fastener clamping two layers of living tissue 18 which include a proximal layer 14 and a distal layer 16 of tissue. The fasteners described herein, however, can fasten any type of materials together, such as a graft or synthetic fibers which may be used as a substitute for tissue, or a combination thereof. The synthetic fibers, for example, may be a material such as Gore-Tex, Dacron or Teflon. Autogenous and non-autogenous human tissue, as well as animal tissue, may also be used.

For all fasteners described above, the leading end 21 of the fastener, shown in FIG. 2, can be sharpened for ease of penetration either by cutting the wire on a bias or by tapering the end to a sharp point during manufacture of the fastener. The bias cut is commonly used to make sharp points on conventional staples and taper pointing is used to make a certain class of suture needles. Both techniques are well known to those skilled in the art. Other sharpening techniques, such as trocar points, may also be effectively applied to the fastener. Alternatively or additionally, a tube 154 of a delivery instrument 150 that houses the fastener, as shown in FIGS. 5A–5F and 6A–6F, can have a sharpened tip which is used to penetrate the tissue 18 prior to pushing the fastener from said tube. All such variations are referred to herein as "needle assemblies".

A wide variety of fasteners can be designed within the scope of this invention for an equally wide variety of fastening purposes. Some of these shapes are shown in FIGS. 1A–4 and it should be apparent that other variations are both possible and likely as the invention becomes more widely applied.

The surgical fasteners described herein can also be used in applications that require the insertion of a fastener from the interior. For example, the fasteners can be used in endovascular procedures to attach a graft within large vessels such as the aorta or iliac arteries to repair aneurysms or occlusions.

FIGS. 5A–5F show a first embodiment of a delivery instrument 50 and the method for inserting the fastener. The delivery instrument 50 consists of a plunger 52 having a head portion 60, a needle 54 having a head portion 55, and a sleeve 51 having a head portion 57 and a stop 56. The plunger 52 fits slidingly inside a lumen of the needle 54, which fits slidingly inside of the sleeve 51. FIGS. 5A–5F show the fastener 10 being used to attach a graft (tissue; lower membrane) 16 to a blood vessel having a first layer of tissue 14 and an opposite wall 17. The fasteners described herein, however, can be used for any layers of material or tissue. Furthermore, the delivery instrument 50 can deliver any of the fasteners described herein.

Depending on the situation, support for the lower membrane 16 will be required in order to insert the fastener 10. This normally will be the rigidity of the body tissue itself or a mechanical support which is provided separately, often as an integral part of the instrument that deploys the graft.

For the delivery instrument shown in FIGS. 5A–5D, the head portion 60 of the plunger 52 has two stops 62, 64 attached to it. One of the stops 62 pivotally engages the head portion 55 of the needle 54 and also pivotally engages a stop 56 of the head portion 57 of the sleeve 51. The other stop 64 can engage the head portion 55 of the needle 54. These stops 62, 64 are used to control the amount of depth that the needle and/or fastener may be inserted into the tissue 18.

Figures 5A, 5B, 5C:
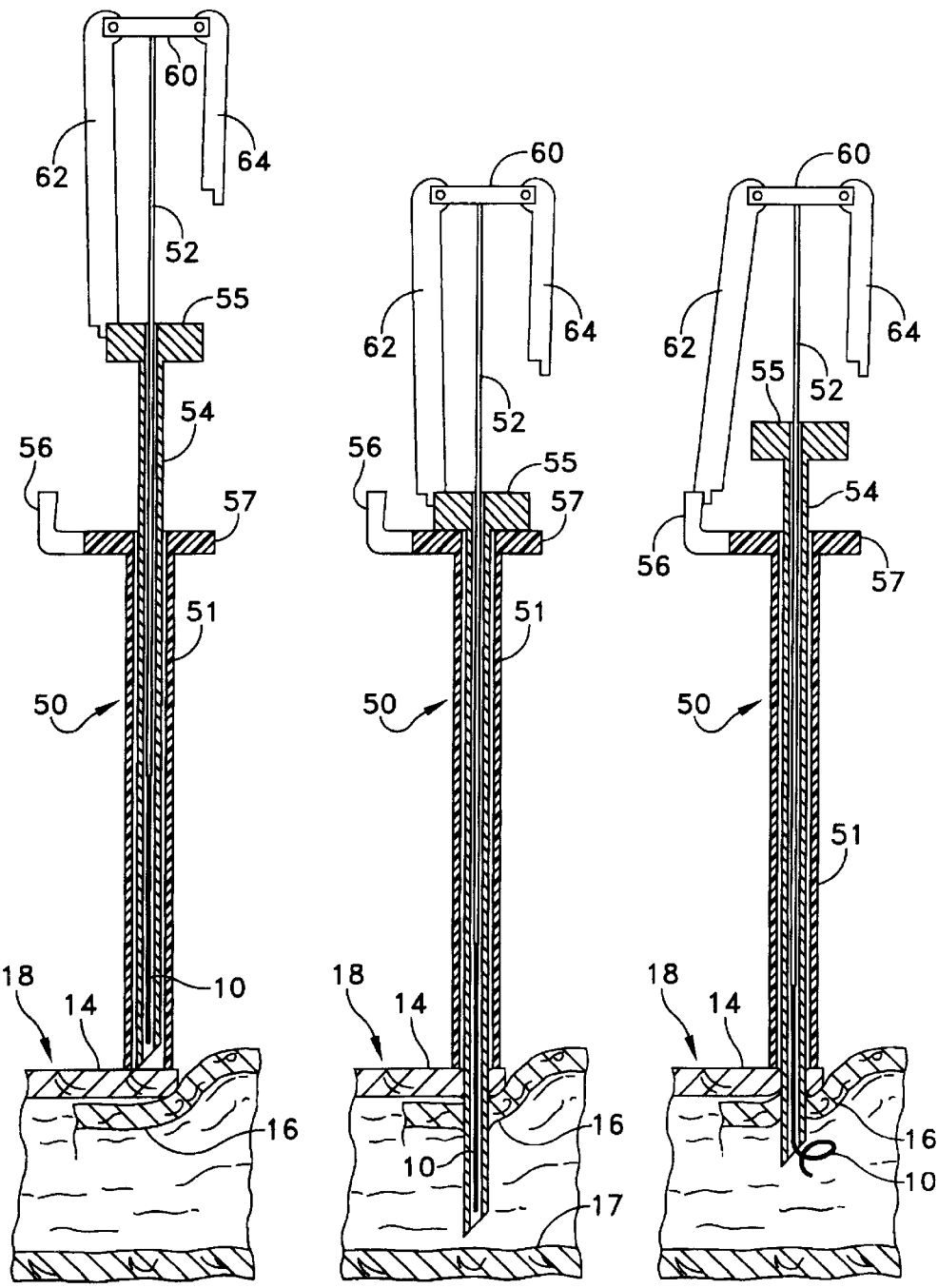

In FIG. 5A, the delivery instrument is shown ready to insert a fastener 10 into layers of tissue 18 with the tip of the instrument 50 placed against the tissue. First, the stop 62 is engaged against the head portion 55 of the needle 54, such that the needle 54 and plunger 52 can be inserted into the tissue 18 in unison. The needle 54 and plunger 52 are inserted until the head portion 55 of the needle 54 rests upon the head portion 57 of the sleeve 51, as shown in FIG. 5B. It should be apparent that if the needle 54 is inserted into a blood vessel, as shown in FIGS. 5A–5D, care should be taken not to insert the needle past the opposite wall 17 of the vessel.

In FIG. 5C, the stop 62 is swung to engage the stop 56 on the sleeve 57. This will enable the needle 54 to be raised while the plunger 52 remains still. While the needle 54 is withdrawn, the restraining force of the needle 54 upon the fastener 10 is removed and the fastener begins to form in its unstressed and undeformed shape.

In FIG. 5D, the needle 54 is raised until its head portion 55 engages stop 64. When the needle head portion 55 engages stop 64, a doctor can be certain that the needle has exited the layers of tissue 18. The lower portion of fastener 10 will now have formed itself in the shape of a coil.

In FIG. 5E, the stop 64 is swung away from the head portion 55, such that the needle 54 can be withdrawn fully. As shown, the fastener 10 begins to form in its unstressed shape as the needle 54 is removed.

FIG. 5F shows the full withdrawal of the deployment instrument 50. The fastener 10 can now fully assume its unstressed shape. It should be noted that the unstressed coils of the fastener 10 shown in FIGS. 5D through 5F are shown having an exaggerated shape for the sake of clarity. The fastener 10 more accurately would appear as shown in FIG. 1C with the coils exerting a compressive pressure upon the layers of tissue 18.

FIGS. 6A through 6F show a second embodiment of the delivery instrument 100 which can deliver any of the fasteners described herein. The plunger 102 has a head portion 110 having both a short stop 114 and a long stop 112 attached to it. The head portion 105 of the needle 104 has two slots 116 and 118 to accept the long 112 and short 114 stops, respectively, at different times of the process. The needle 104 is slidingly accepted by sleeve. 101 having a head portion 107. The tip of the delivery instrument 100, fastener 10 and needle 104 for FIGS. 6A–6F appear the same as in FIGS. 5A–5F, respectively, and are not shown for the sake of clarity.

First, as shown in FIG. 6A, the long stop 112 is brought into contact with the head portion 105 of the needle 104. The plunger 102 and needle 104 are then inserted into the tissue in unison by pushing down in the direction of arrow 120 until the needle's head portion 105 comes into contact with the sleeve's head portion 107, as shown in FIG. 6B. The needle 104 and fastener have penetrated the layers of tissue.

The head portion 110 of the plunger 102 is then rotated as shown in FIG. 6C in the direction of arrow 122 until the long stop 112 can be inserted into slot 116. The needle's head portion 105 is then raised in the direction of arrow 124 (FIG. 6D) until the needle's head portion 105 comes into contact with the short stop 114, as shown in FIG. 6D. In FIG. 6D, the needle 104 will be fully withdrawn from the layers of tissue.

In FIG. 6E, the plunger's head portion 110 is rotated in the direction of arrow 126 until the short stop 114 can be inserted into slot 118. The needle's head portion 105 is then fully raised in the direction of arrow 128 (FIG. 6F) until the head portion 105 comes into contact with the plunger's head portion 110. The needle 104 is now fully retracted from the fastener which should be fastened in the tissue and formed in its unstressed state.

It should be apparent that many types of stops could be used to position the needle 54, 104 and plunger 52, 102 of the delivery instruments 50, 100, 150. For example, the needle could function with only a single stop attached to the shaft of the plunger. Alternatively, visual indicators could be used, but would be inherently less reliable. It should be apparent that the delivery instruments as shown in FIGS. 5A–5F and 6A–6F, could function properly without the short stops 64, 114, but not as reliably. Also, the delivery instruments, as shown in FIGS. 5A–5F and 6A–6F, could function without the sleeve 51 or 101, respectively. It should be apparent that a plurality of any of these delivery instruments described herein could be integrated in a single delivery instrument for sequential or simultaneous delivery of the fastener.

Figure 7:
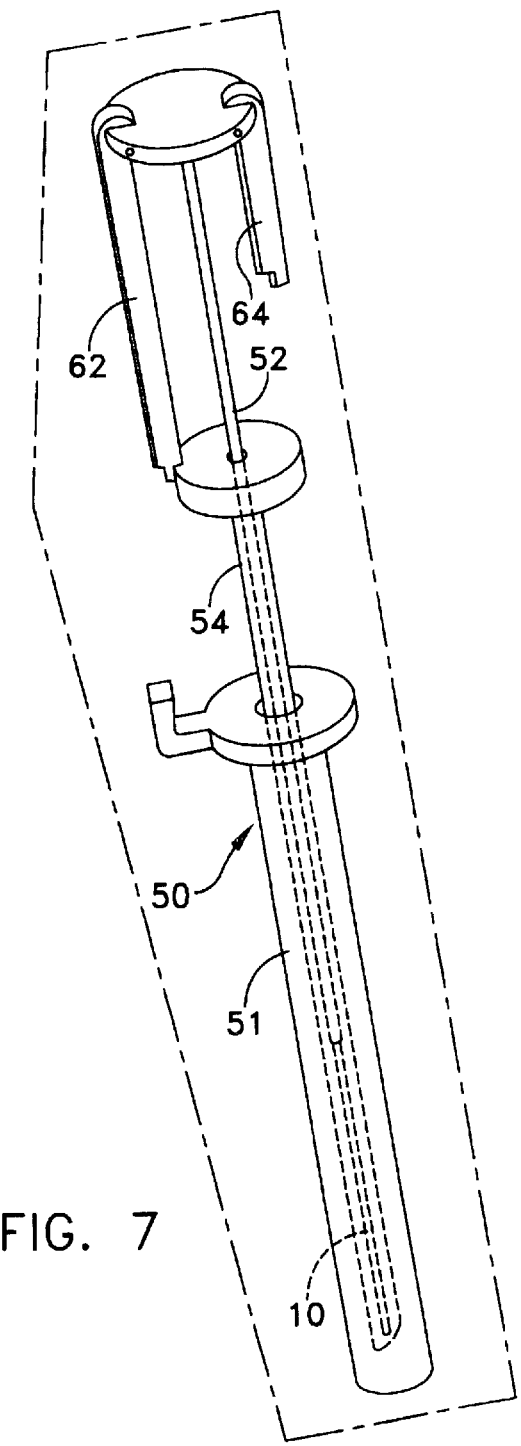
FIG. 7 is a front isometric view of the deployment instrument of FIGS. 5A–5F as it is shipped.

FIG. 7 shows the delivery instrument 50 as it might be shipped from a manufacturer. The surgical fastener 10 preferably is already inserted and straightened inside of the needle 54 for ease of use. The delivery instrument 50 can be shipped with or without the sleeve 51, which can be added later when the fastener is ready to be inserted.

Figure 8:
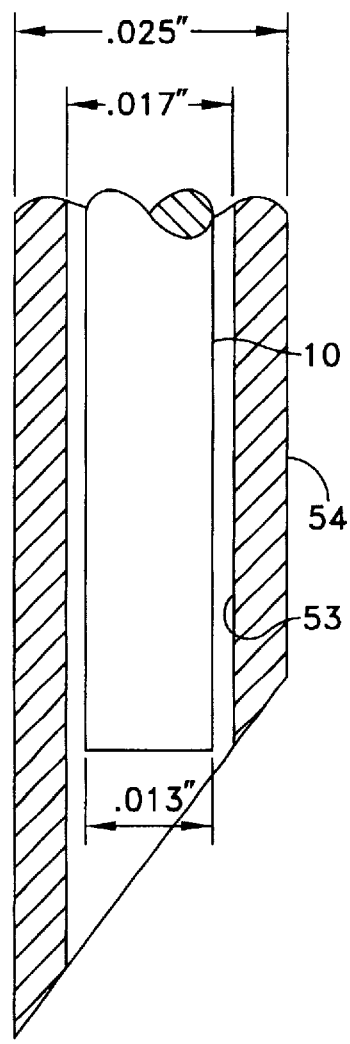
FIG. 8 is a front cutaway view of the deployment instruments of FIGS. 5A–5F and 6A–6F.

FIG. 8 shows an enlarged view of the needle of either FIGS. 5A–5F or 6A–6F with a fastener inside of it. A typical aspect ratio of the length to diameter for this device can be in the order of 40 or 50 for less invasive use. The diameter of the fastener is preferably between 0.012 to 0.014 of an inch, more preferably its diameter is 0.013 of an inch, the inside diameter of the lumen 53 of the needle 54 is preferably 0.017 of an inch and the outside diameter of the needle is preferably 0.025 of an inch.

FIGS. 9A–9D show a third embodiment of the delivery instrument 150 and the method for inserting the fastener. The third embodiment of the delivery instrument 150 is different from the first two embodiments in that a restraining tube 154 is not sharpened to penetrate tissue. Thus, the surgical fastener 20 used with the deployment instrument 150 should have a sharpened end to penetrate tissue. The delivery instrument 150, consisting of slender tubes and rods, is inherently small in diameter compared to its length. Thus, FIGS. 9A–9D are illustrated with a much less favorable aspect ratio for the sake of clarity. A typical aspect ratio of the length to diameter for this device can be in the order of 40 or 50 for less invasive use. It should be apparent that other ergonomically sophisticated designs for the deployment instrument 150 can be envisioned and realized. It should also be apparent that several of these deployment instruments could be integrated in a single deployment instrument 150 for sequential or simultaneous deployment of the fastener.

FIG. 9A shows a delivery instrument 150 resting on layers of tissue 18 to be joined. The delivery instrument 150 restrains a fastener by placing stress upon it. The fastener 20, which in this example is the fastener of FIG. 1, resides in a substantially straightened form entirely within the restraining tube 154. It should be apparent that any of the fasteners described herein if given a pointed end 21 can be used with the delivery instrument of FIGS. 9A–9D. The pointed end 21 of the fastener 20 is facing toward the tissue. A plunger 152 rests on the fastener 20 and is configured to push the fastener partially out of the restraining tube 154 until the plunger 152 stops against a shield 156, as shown in FIG. 9B.

FIG. 9B shows the fastener 20 partially installed by the plunger 152. As the fastener emerges from its restraining tube, the fastener penetrates the proximal 14 and distal 16 layers of tissue and gradually assumes the remembered shape of its lower coil, piercing the distal tissue layer 16 again as it turns upward. The lower coil 24 of the fastener 20, however, preferably remains substantially on the distal side of the tissue. At this point, plunger 152 bears on the shield 156 and can progress no further. Depending on the clinical application, it may be necessary to support the tissue 18 distally during penetration.

FIG. 9C shows restraining tube 154 moving upward, gradually freeing the fastener 20 to assume its remembered shape. It will obviously not be able to do so until the restraining tube 154 is completely clear, which happens when the restraining tube stops against plunger 152. The restraining tube 154 tends to pull the fastener 20 out of the tissue due to friction producing forces exerted by the fastener on the restraining tube as the former tries to assume its remembered shape. This tendency is offset by the plunger 152 bearing on the upper end of the fastener 20 as the restraining tube 154 moves upward.

FIG. 9D shows restraining tube 154 in its fully upward position as determined by the plunger 152. The restraining tube 154 has cleared the fastener 20 and allowed it to assume its remembered, coiled shape 22, bearing against the tissue 18. The fastener 20 forms within a guide tube 151, suggesting that the guide tube 151, properly shaped, may serve to guide the fastener 20 as it forms above the tissue 18. This may be a useful feature, especially for more complex fasteners which may re-form incorrectly when released from constraint.

The guide tube 151 can serve a dual function as described above, providing a reference stop for plunger 152 and a forming guide for the fastener 20. In some cases the guide tube 151 will not be required.

Referring to FIGS. 10 and 11, it will be seen that a graft 158 of the type joined to the aorta includes a body 160 which is typically 10 mm in diameter, and a flange 162 on one end 164 of the body 160, the flange 162 being formed by altering the weaving, or knitting program, or by molding or stretching the body of the graft, depending on the graft material, which may be synthetic material or natural tissue, including harvested tissue. The flange 162, which is about 2–2½ times the body diameter is used to anchor the graft 158 to the inside of the aorta wall 166. In a preferred embodiment, the plane of the flange 162 is located at an acute angle (FIG. 2) to the longitudinal axis of the body 160. This encourages the body 160 of the graft 158 to lie along the aorta, rather than protrude normal to it. This is generally a desirable orientation for subsequent routing of the graft 158 to a distal destination without accidentally crimping the graft or interfering with other anatomical structures.

The delivery instrument 170 which deploys the graft 158 is a device somewhat analogous to an umbrella frame which, when collapsed, supports the graft, suppresses the flange 162, and transports it through a previously prepared opening in the aorta. Once deployed, arms 172 of the tool 170 extend, restoring the flange 162 and supporting it during attachment to the aorta wall 166. After the graft is attached, the arms 172 of the instrument 170 retract, allowing the instrument to be retraced axially through the lumen 168 of the graft.

Referring to FIG. 12, it will be seen that the aforesaid delivery instrument 170 initially resides in the lumen 168 of the graft 158. The flange 162 is forced to the diameter of the graft body 160 by pivoting arms 172 which are positioned to enter throughout a hole 176 in the aorta. The flange 162 of the graft 158 is retained via abutments 174 on the pivoting arms 172 which fit into holes 178 in the flange 162. A retainer 180 is positioned to lock the arms 172 in the extended position.

Figure 14:
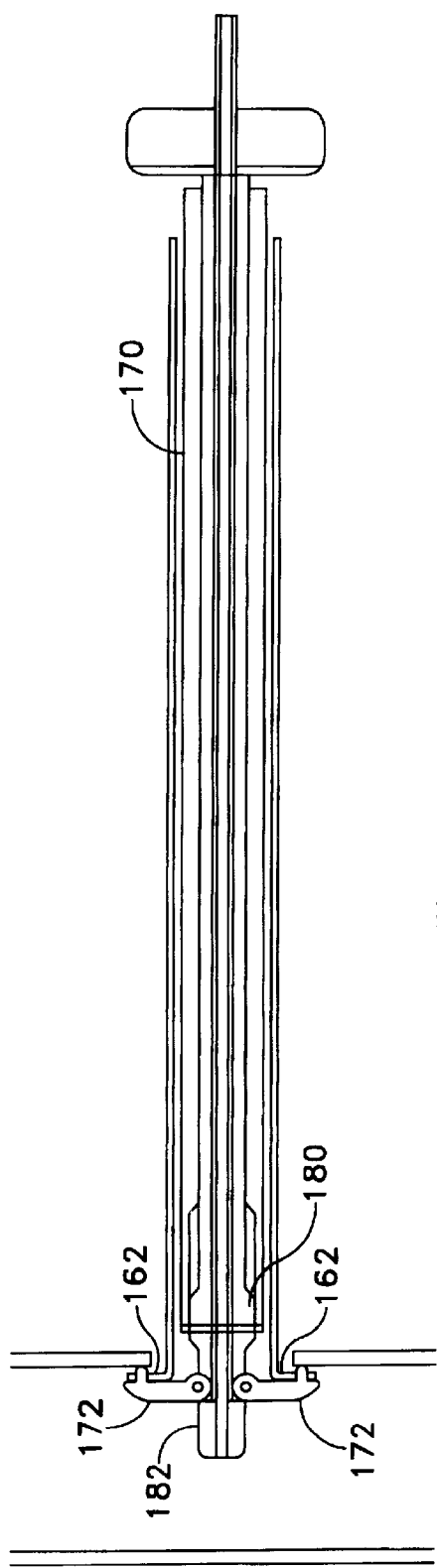

In FIG. 13 the graft flange 162 has been pushed into the aorta by the instrument 170. In FIG. 14 the graft flange 162 is deployed by pivoting the arms 172 of the instrument outward 90°. This is accomplished by releasing the retainer 180 and moving a cam 182 to the left, as viewed in FIG. 14. The cam 182 locks the arms 172 in the position shown in FIG. 14.

At this time, fasteners as described hereinabove are introduced to attach the flange 162 to the wall of the aorta. The force to install the fasteners is countered by the instrument which is pulled to the right, as viewed in FIG. 14, to hold the graft 158 firmly against the wall of the aorta.

The fasteners can be applied individually as described hereinabove to minimize the total force applied to the tissue at any time.

Figure 16:
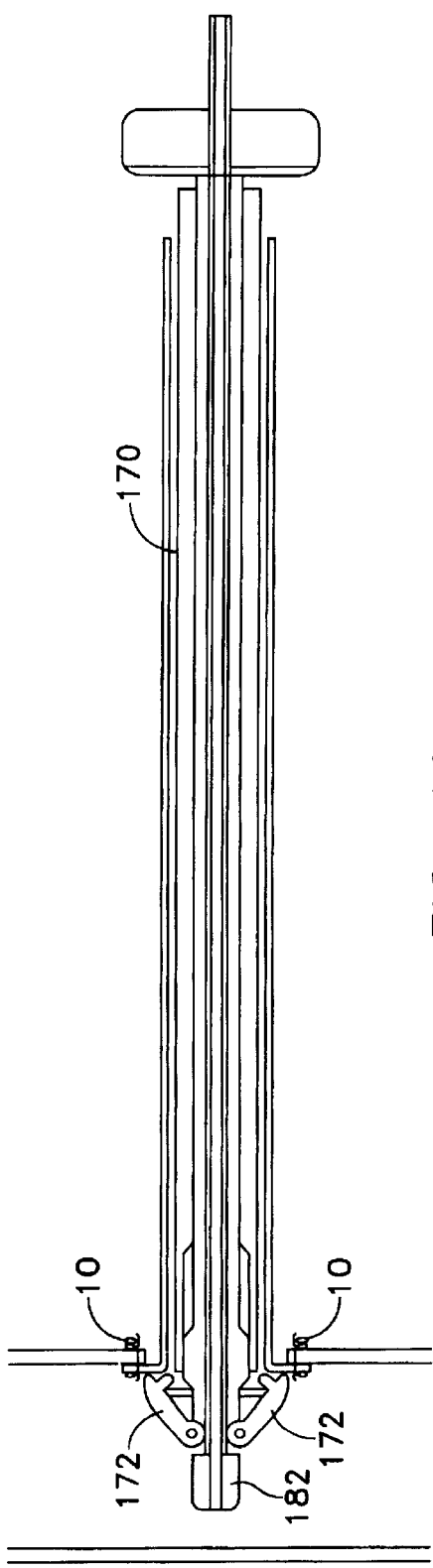
Figure 15:
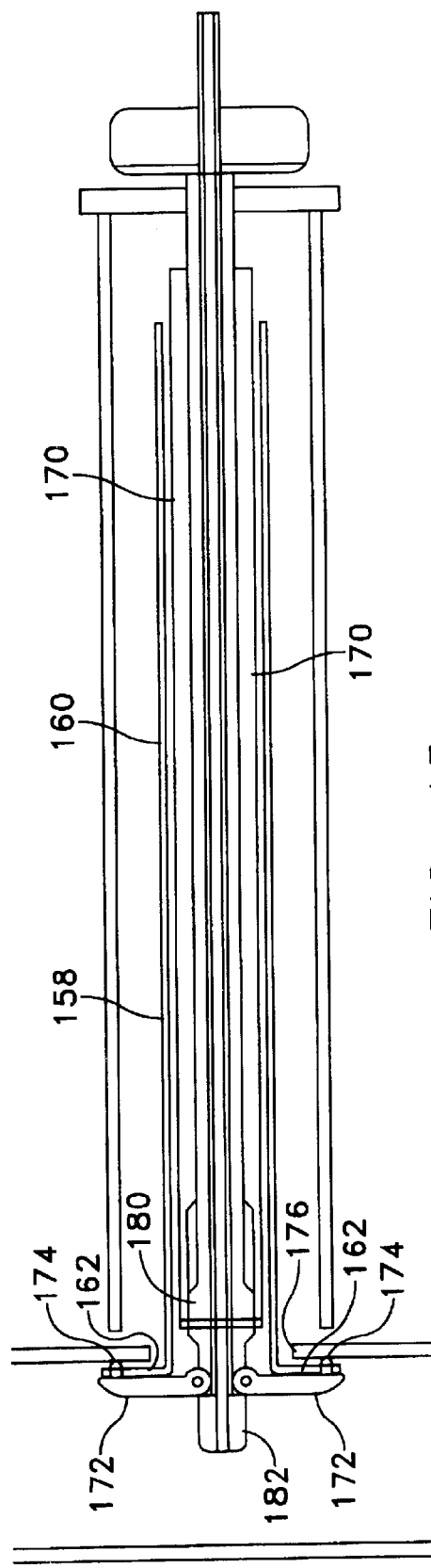

In a preferred embodiment (FIG. 15) the fasteners are arrayed in a precise relationship to one another and located on the delivery instrument 170 in precise relationship to the flange 162. The fastener deployment means may be integral with other operating controls of the delivery instrument. FIG. 16, after the fasteners 10 have been deployed, cam 182 is released and moved leftward, as viewed in FIG. 16, allowing arms 172 to pivot as the instrument is moved further into the aorta. As this happens, the arms 172 gradually disengage form the holes 178 in the graft flange. In FIG. 16, the retainer 182 moves leftward to fully extend arms 172 (FIG. 17).

Figure 17:
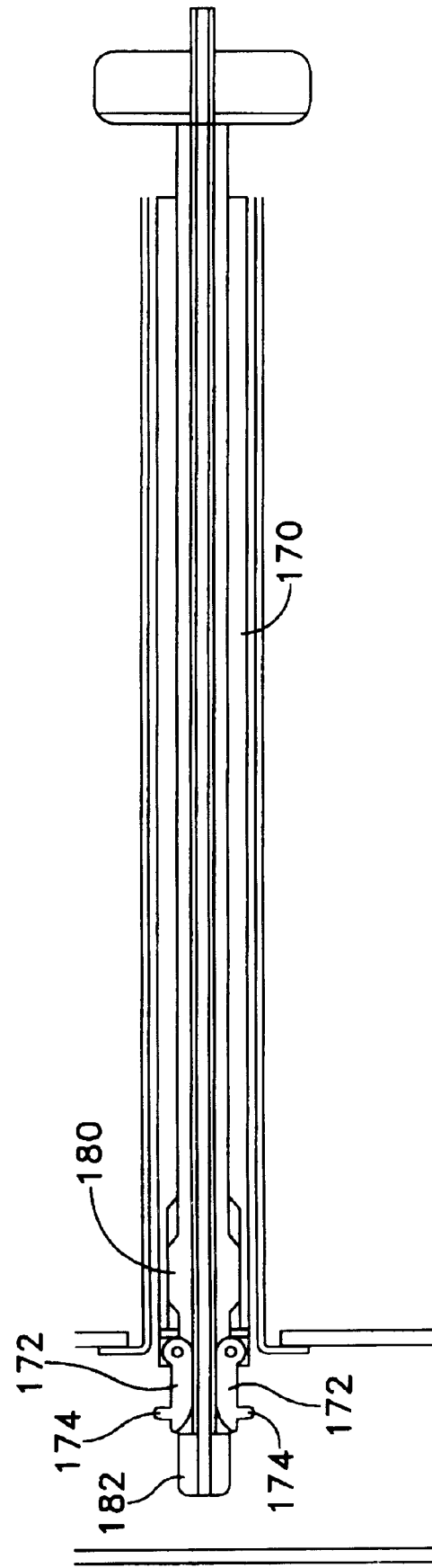
Figure 18:
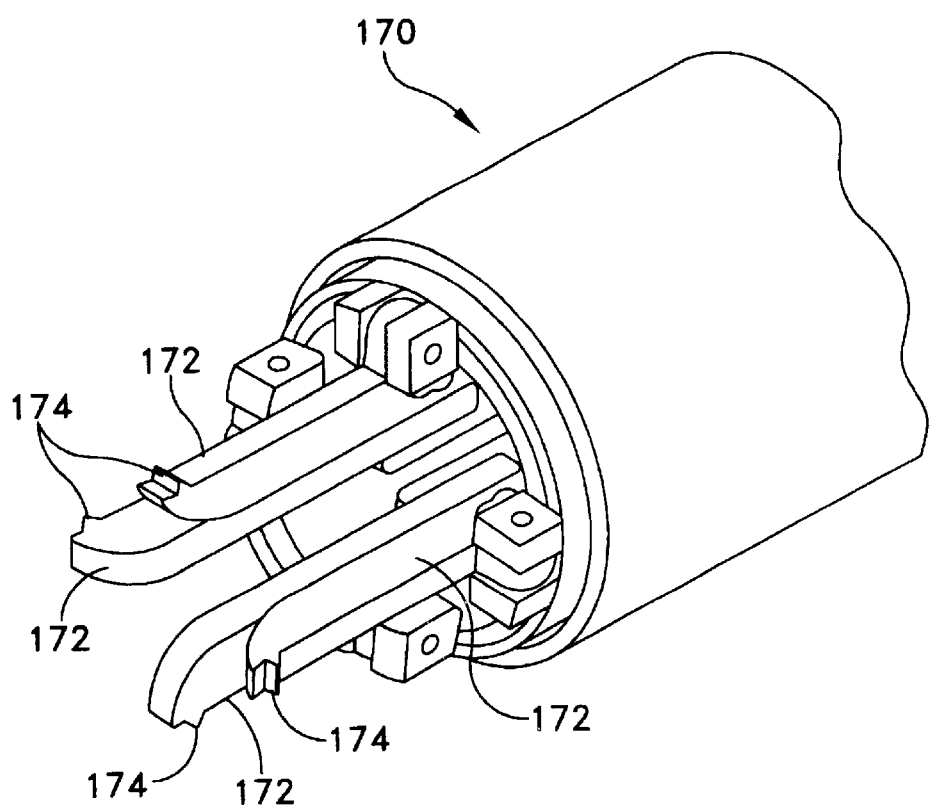
FIG. 18 is an enlarged perspective view of a portion of an instrument used for effecting the attachment of a graft to an aorta.

At this,point, the instrument can be removed from the graft by pulling to the right, as viewed in FIG. 17. The instrument will obviously have a set of ergonomic controls at its proximal end to manipulate the cams and fasteners. These controls can assume a variety of useful forms and can be designed in a variety of ways, all of which are obvious to one skilled in the art and which fall within the scope of this disclosure.

The above-described devices permit use of a clinical protocol which minimizes blood loss without clamping the aorta. The procedure uses a variety of standard devices in conjunction with the invention to implement the procedure as described hereinabove.

Figures 19, 20, 21, 22:
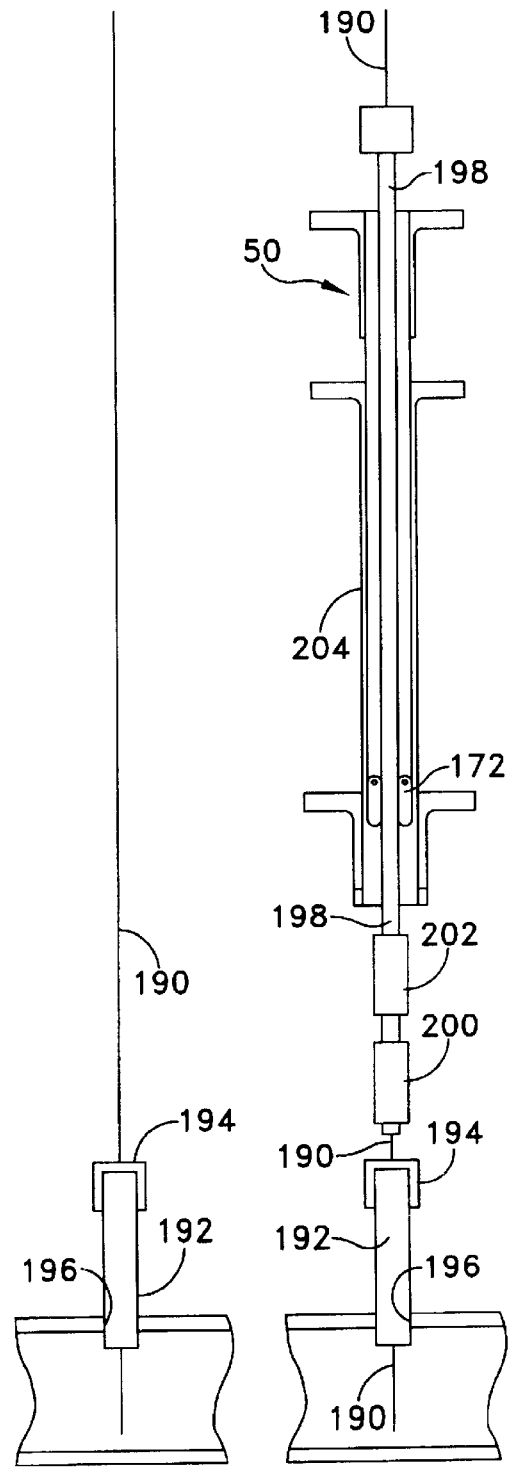
Figure 23:
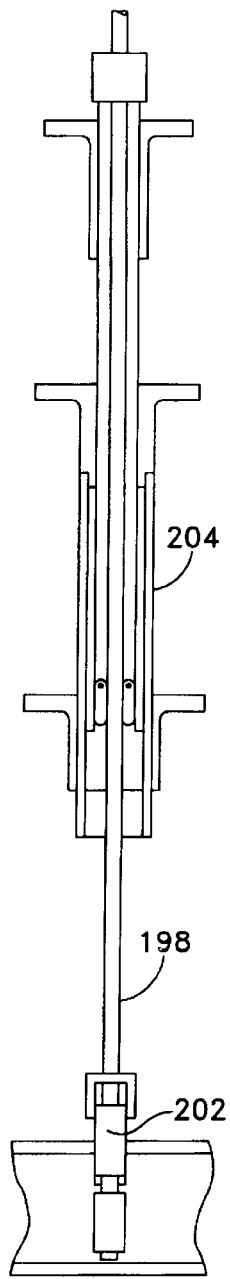

Referring to FIG. 19, it will be seen that an exposed artery A is punctured at the graft site with a needle 184 (18–20 gage), having a removable core (not shown). The core is replaced with a flexible guidewire 190 which is inserted a short distance into the artery A and the needle 184 is removed, leaving the guidewire 190 in place (FIG. 20).

A sheath 192 with hemostatic valve 194 is introduced over the guidewire 190 and forced into the artery (FIG. 21), dilating the guidewire opening 196, as required. The guidewire 190 remains in place.

A temporary safety balloon catheter 198 is inserted over the guidewire 190 and through the sheath 192 (FIG. 22). Both the guidewire 190 and the balloon catheter 198 are passed through a central channel in the sheath 192 before placement into the aorta. The catheter 198 is a dual balloon catheter, with both balloons 200 and 202 preformed and non-compliant. The safety balloon 200, with a large diameter and short length (40 mm×10 mm) when inflated, assumes the shape of a flattened disc (not shown), and is placed at the most distal end of the catheter 198. The dilation balloon 202, 10 mm in diameter and 80 mm long, assumes a more elliptical shape (FIGS. 24 and 25) and is placed more proximally. Separate inflation ports, one suitable for rapid inflation, would be placed at the external end of the catheter 198. Should bleeding occur, the safety balloon 200 would be rapidly inflated and pulled up against the aortic wall, sealing the hole 196 in the aorta until proper surgical control is achieved.

The sheath 192 is removed and the dilating balloon 202 is inflated (FIG. 24) to create an arteriotomy, which is a permanent opening in the wall of the aorta approximately 10 mm in diameter to accommodate the graft.

Figure 25:
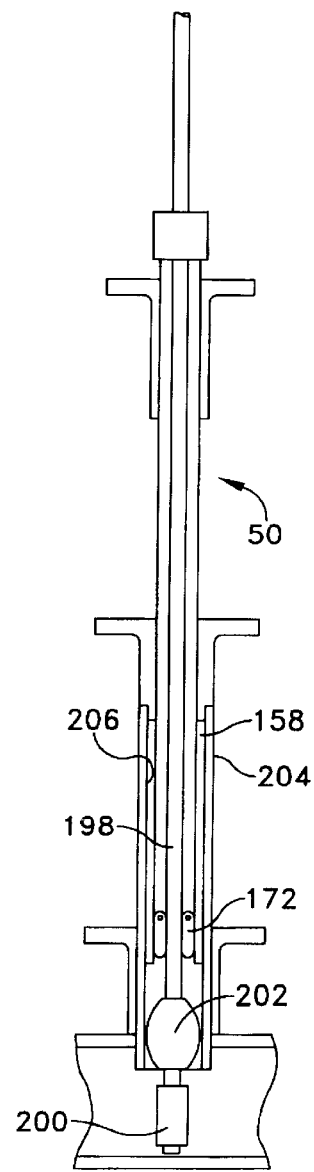

A sheath 204 has within it the graft 158 and the graft delivery system 50 (FIG. 25). At its external end there is a hemostatic valve (not shown) preventing leakage of blood out the catheter. In its center there is an inner channel 206 for passage of the guidewire and dual balloon catheter 198. At the internal end, the sheath 204 is free of the graft and the graft delivery system so that this portion of the sheath 204 can be inserted over the fully inflated dilating balloon 202 into the aorta (FIG. 25). Once inserted, the dilating balloon 202 is deflated. The safety balloon 200 remains in place uninflated for use in an emergency.

Figure 29:
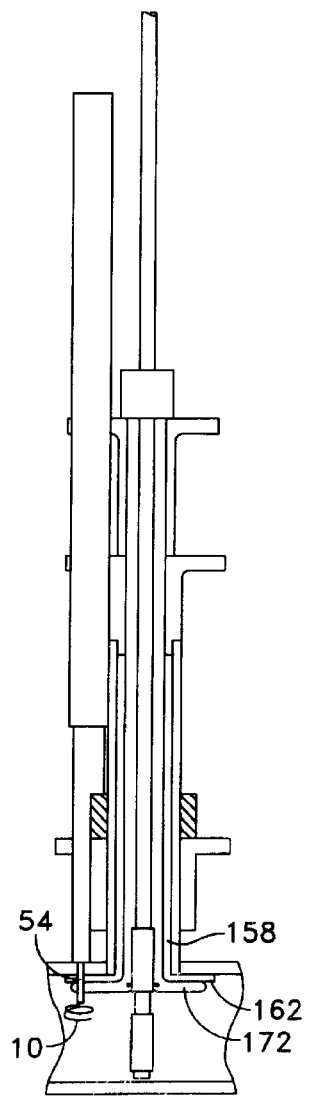
Figure 30:
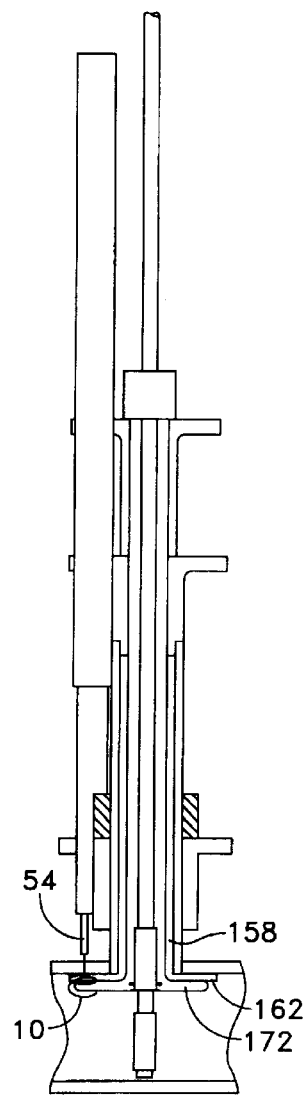
Figure 31:
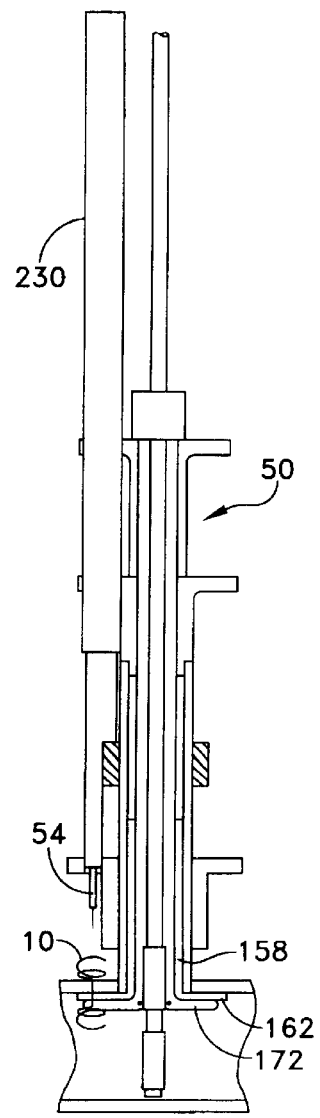

The delivery instrument 50 with graft 158 as described previously, is inserted into the working sheath 204. The graft 158 is then advanced into the aorta A (FIG. 26), the graft flange 162 thereof is spread outwardly by the arms 172 (FIG. 27), and the fasteners 10 are introduced by the needle or needles 54 (FIGS. 28–31) to effect attachment of the graft 158 to the aorta A (FIGS. 29 and 30). The needle assembly is then withdrawn (FIG. 31).

Figure 32:
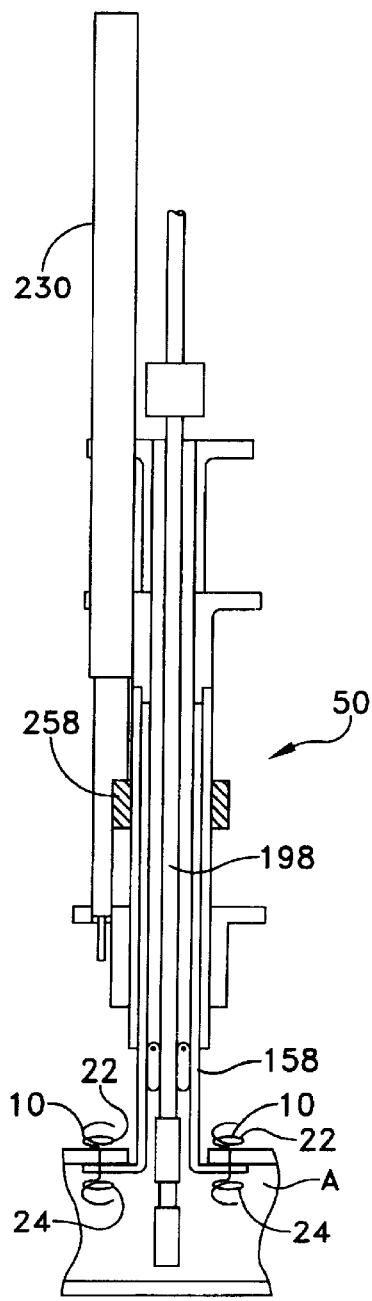
Figure 33:
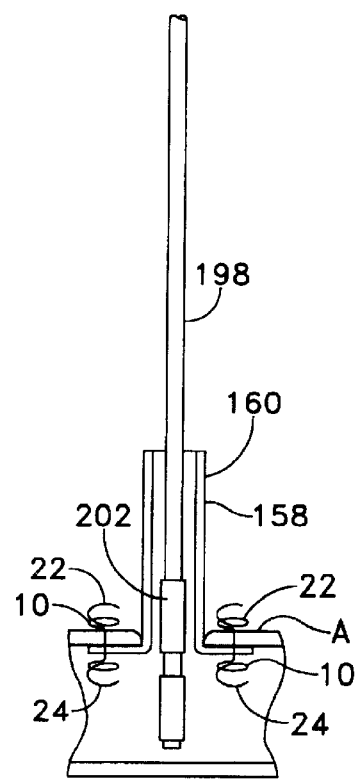

After successful attachment of the graft 158 to the aorta (FIG. 32), the entire instrument is withdrawn (FIG. 33). At that time, blood would be flowing though the attached graft 198 and a graft occlusion device is necessary. The dilation balloon 202 would then be inflated (not shown) to occlude the graft body 160 until a standard arterial clamp could be placed externally on the graft to ensure hemostasis. The dual balloon catheter is then withdrawn.

As the instrument 50 and working sheath 204 are removed, the safety balloon 202 is inflated and held against the lumen 168 of the graft body 160. The graft is clamped as the safety balloon is deflated and removed, completing proximal connection of the graft. The graft is then extended by anastomosis, if necessary, and routed to its distal destination, using a proximal clamp on the graft to control blood flow during the procedure.

Figure 34:
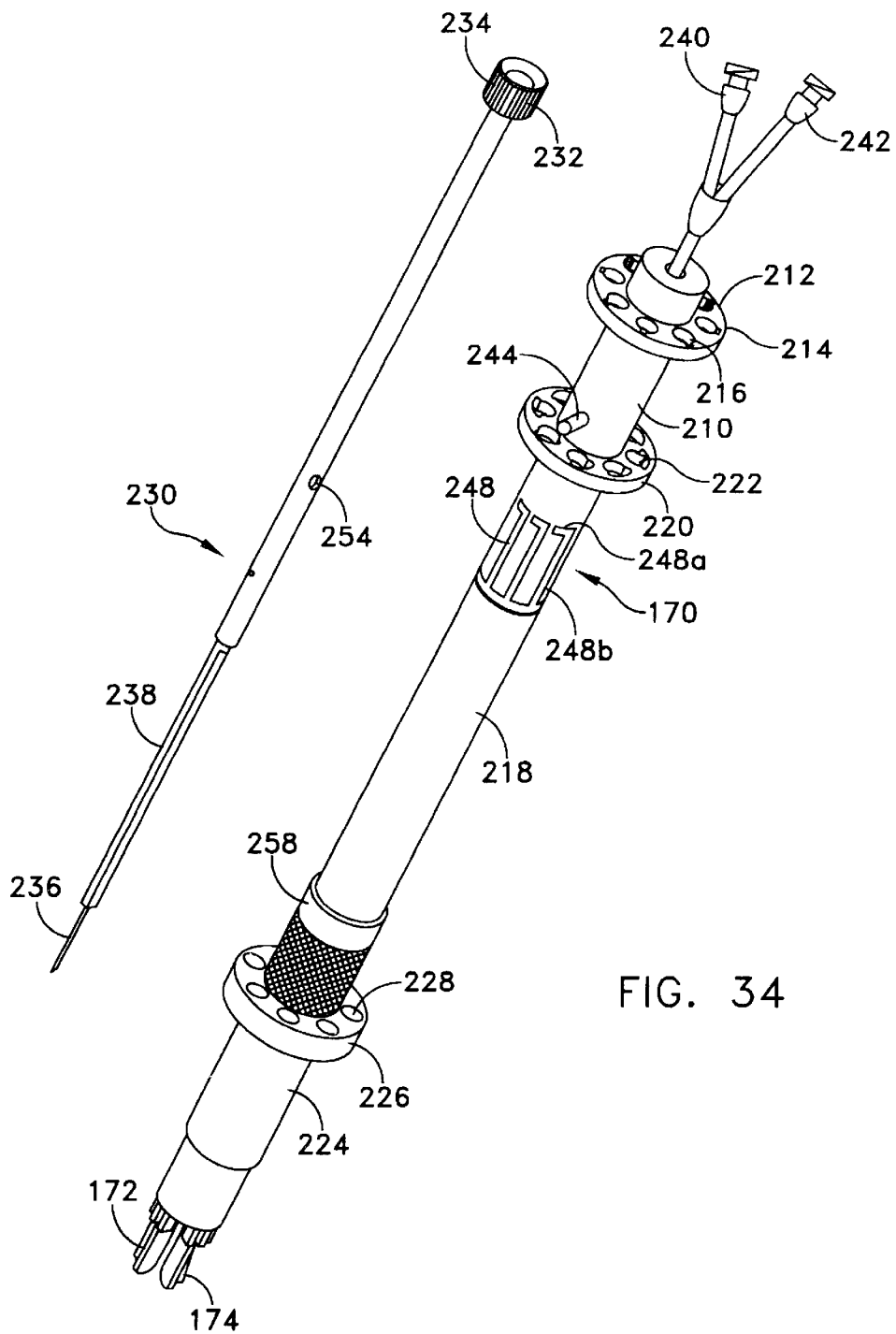

Referring to FIG. 34, it will be seen that the delivery instrument 170 may be provided with a plunger 210 having a head portion 212 comprising an annular flange 214 having a series of apertures 216 therein. Similarly, sleeve 218 in which the plunger 210 is disposed, is provided with an annular flange 220 having apertures 222 therein aligned with the apertures 216 in the flange 214. A further sleeve 224 is similarly provided with an annular flange 226 having apertures 228 therein aligned with the apertures 222 of the flange 220.

Each series of aligned apertures 216, 222, 228 retains a needle assembly 230 which includes a needle head 232 having gear teeth 234 thereon. Each needle assembly 230 (one shown in FIG. 34), constitutes a carrier for a suture element 236 and a pusher element 238 for pushing the suture element 236 out of the needle and into the aorta, as described hereinabove. Each needle assembly is provided with an outwardly-extending detent 254.

Figure 24:
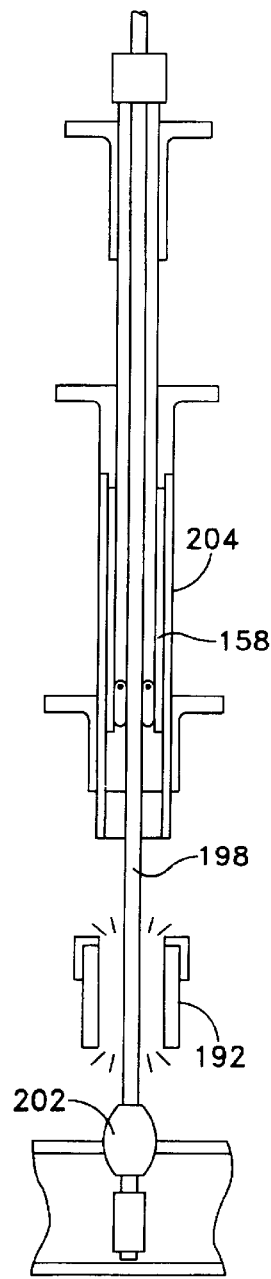

Inlets 240, 242 are provided for admitting fluid to the balloons 200, 202 (FIGS. 24 and 25).

To facilitate step-by-step movements of the components as described hereinabove, the plunger 210 is provided with a stop detent 244 which is engageable with the flange 220, and the needle assembly 230 is provided with a detent 246 disposed in a slot 248 in the sleeve 218. A lever 256 (FIG. 35) extends outwardly through the circle of needle assemblies 230 and is used to effect axial movement of a collar 258 to effect withdrawal of needle assemblies 230 from the graft flange suture area.

The needle heads 234 are disposed in a cap member 250 (FIGS. 35–38) having internal threads 252 which engage the needle head gear teeth 234. As is illustrated in FIG. 37, turning of the Gap member 250 serves to rotate each of the needle assemblies 230 around the axis thereof, to move the needle assembly detents 254 along width-wise portions 248a of the slots 248 and into length-wise portions 248b of the slots 248, which permit lengthwise movement of the needle assemblies 230.

It will be apparent that the alternative embodiment of FIGS. 34–38 permits suturing in a plurality of loci, around the aorta hole 176 and on the graft flange portion 162, simultaneously, thereby substantially reducing the time required for suturing the graft to the aorta.

It should be appreciated that the present invention may be used to attach a graft to an aorta, or to attach a graft to some other vascular structure, or to attach a graft to some other tubular structure (e.g., intestine, lymph node, etc.) and in other ways which will be apparent to those skilled in the art.

It should be understood that the foregoing is illustrative and not limiting and that obvious modifications may be made by those skilled in the art without departing from the spirit of the invention. Accordingly, reference should be made primarily to the accompanying claims, rather than the foregoing specification, to determine the scope of the invention.

What is claimed is:

1. An instrument for attaching a graft to an aorta or other tubular structure, the instrument comprising:
    a first needle assembly for breaching the aorta to provide a hole in a wall thereof;
    a carrier portion for insertion of an end of a tubular graft through the hole and into the aorta;
    arms pivotally mounted on the instrument and moveable from a position extending axially of said carrier to a position extending radially from said carrier to spread the end of the tubular graft radially outwardly from a tubular body portion of the graft to form a generally annular flange portion extending outwardly from the tubular body portion, and to support the flange portion within the aorta and around the hole therein; and
    a second needle assembly adapted to retain a coil fastener therein and to advance said coil fastener into engagement with the aorta wall and the graft flange portion for attaching the graft flange portion to the aorta wall.

2. The instrument in accordance with claim 1 wherein said second needle assembly includes a coil fastener needle for penetrating the aorta and the graft flange portion.

3. The instrument in accordance with claim 2 wherein the coil fastener is disposed in the coil fastener needle and exits the suture needle to engage the aorta wall and the graft flange portion.

4. The instrument in accordance with claim 1 wherein said second needle assembly includes a tube for retaining the coil fastener and the coil fastener is provided with a sharp distal end for penetrating the aorta and the graft flange portion.

5. The instrument in accordance with claim 1 wherein said flange portion of said graft is provided with holes therein and said arms are provided with abutments which engage the holes to carry the graft into the aorta.

6. An instrument for attaching a graft to an aorta or other tubular structure having a hole in a wall thereof, the instrument comprising:
    a carrier portion for insertion of an end of a tubular graft through the hole and into the aorta;
    arms pivotally mounted on the instrument and moveable from a position extending axially of said carrier portion to a position extending radially from said carrier portion to spread the end of the tubular graft radially outwardly from a tubular body portion of the graft to form a generally annular flange portion extending outwardly from the tubular body portion, and to support the flange portion within the aorta and around the hole therein; and
    a needle assembly disposed on the instrument and adapted to retain a coil fastener therein and to advance said coil fastener into engagement with the aorta wall and the graft flange portion for attaching the graft flange portion to the aorta wall.

7. The instrument in accordance with claim 6, wherein said carrier portion is provided with a stop for preventing the carrier portion from extending through the aorta to a wall opposite the hole.

8. The instrument in accordance with claim 6 wherein said carrier portion is provided with a balloon member adapted for expansion to fill the hole.

9. The instrument in accordance with claim 6 wherein in addition to said needle assembly disposed on the instrument, at least one further needle assembly is disposed on the instrument and adapted to attach the graft flange portion to the aorta wall simultaneously with said needle assembly.

10. The instrument in accordance with claim 9 wherein said needle assemblies comprise a circular array of needle assemblies operable to simultaneously effect attachment of the graft flange to the aorta wall around the hole.

11. A method for fixing a graft to an aorta or other tubular structure, the method comprising the steps of:
    providing a graft having a tubular body portion and an annular flange portion at one end of the tubular body portion;
    providing an instrument having a first needle assembly for breaching the aorta, for positioning the flange portion of the graft adjacent a wall of the aorta, and for suturing the graft flange portion to the aorta;
    mounting the graft in the instrument;
    mounting a second needle assembly, supporting suturing material, on the instrument;
    operating the instrument to breach the aorta to provide a hole therein;
    operating the instrument to move the graft to engage the aorta around the hole with the graft flange portion;
    operating the instrument to provide anvil support to the graft flange portion within the aorta; and
    operating the instrument to effect suturing of the graft flange portion by the second needle assembly onto the aorta around the hole in the aorta.

12. The method in accordance with claim 11 wherein the steps of moving the graft to engage the aorta with the graft flange portion, and of providing anvil support to the graft flange portion, comprise moving arms pivotally mounted on a graft carrier portion of the instrument from a position extending axially of the carrier portion to a position extending radially of the carrier portion, the arms thereby spreading the flange portion into the position adjacent the aorta wall.

13. A method according to claim 11 suturing is effected by deployment of a coil fastener.

14. A method for fixing a graft to an aorta or other tubular structure, the method comprising the steps of:

cutting a hole in a wall of the aorta;

providing a graft having a tubular body portion and an annular flange portion at one end of the tubular body portion;

providing an instrument for positioning the flange portion of the graft adjacent the hole and the wall of the aorta, and for suturing the graft flange portion to the aorta;

mounting the graft in the instrument;

mounting a needle assembly, supporting suturing material, on the instrument;

operating the instrument to move the graft to engage the aorta around the hole with the graft flange portion;

operating the instrument to provide anvil support to the graft flange portion within the aorta; and operating the instrument to effect suturing of the graft flange portion by the suture needle assembly onto the aorta around the hole in the aorta.

15. The method in accordance with claim 14 wherein the steps of moving the graft to engage the aorta with the graft flange portion, and of providing anvil support to the graft flange portion, comprise moving arms pivotally mounted on a graft carrier portion of the instrument from a position extending axially of the carrier portion to a position extending radially of the carrier portion, the arms thereby spreading the flange portion and supporting the flange portion in the position adjacent the aorta wall.

16. A method according to claim 14 wherein suturing is effected by deployment of a coil fastener.

17. A method for fixing a graft to an aorta or other tubular structure, the method comprising the steps of:

cutting a hole in a wall of the aorta;

providing a graft having a tubular body portion and an annular flange portion at one end of the tubular body portion;

providing an instrument for positioning the flange portion of the graft adjacent the hole and the wall of the aorta, and for suturing the graft flange portion to the aorta;

mounting the graft in the instrument;

mounting a needle assembly, supporting suturing material, on the instrument;

operating the instrument to move the graft to engage the aorta around the hole with the graft flange portion;

operating the instrument to provide anvil support to the graft flange portion within the aorta; and operating the instrument to effect suturing of the graft flange portion by the suture needle assembly onto the aorta around the hole in the aorta.

18. The method in accordance with claim 17 wherein the steps of moving the graft to engage the aorta with the graft flange portion, and of providing anvil support to the graft flange portion, comprise moving arms pivotally mounted on a graft carrier portion of the instrument from a position extending axially of the carrier portion to a position extending radially of the carrier portion, the arms thereby spreading the flange portion and supporting the flange portion in the position adjacent the aorta wall.

19. The method in accordance with claim 17 wherein the step of cutting a hole in a wall of the aorta is accomplished by a needle having a guidewire therein, and including the steps of inserting the guidewire into the aorta and withdrawing the needle from the guidewire after the cutting of the hole, and mounting the instrument on the guidewire and in part in the hole.

20. The method in accordance with claim 19 and including the step of inserting a catheter into the instrument and on the guidewire, the catheter having a balloon on a distal end thereof, and advancing the catheter on the guidewire to place the balloon at least in part in the aorta.

21. The method in accordance with claim 17 wherein the step of mounting a needle assembly on the instrument comprises mounting a plurality of needle assemblies on the instrument, and the step of effecting suturing comprises effecting a plurality of suturings simultaneously.

22. The method in accordance with claim 21 wherein the plurality of needle assemblies is mounted in circular fashion on the exterior of the instrument and the plurality of suturings is undertaken simultaneously and is disposed in a circle around the hole and in the graft flange and aorta wall.

23. A method according to claim 17 wherein suturing is effected by deployment of a coil fastener.

* * * * *